(12) United States Patent
Ogahara

(10) Patent No.: US 11,554,212 B2
(45) Date of Patent: Jan. 17, 2023

(54) MEDICAL DEVICE

(71) Applicant: TERUMO KABUSHIKI KAISHA, Tokyo (JP)

(72) Inventor: Atsushi Ogahara, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 392 days.

(21) Appl. No.: 16/825,182

(22) Filed: Mar. 20, 2020

(65) Prior Publication Data

US 2020/0215261 A1    Jul. 9, 2020

Related U.S. Application Data

(63) Continuation of application No. PCT/JP2018/031616, filed on Aug. 27, 2018.

(30) Foreign Application Priority Data

Sep. 29, 2017   (JP) .............................. JP2017-191874

(51) Int. Cl.
*A61M 5/145* (2006.01)
*A61M 5/168* (2006.01)
(Continued)

(52) U.S. Cl.
CPC ...... *A61M 5/1452* (2013.01); *A61M 5/16831* (2013.01); *A61M 5/31545* (2013.01);
(Continued)

(58) Field of Classification Search
CPC ............ A61M 5/1452; A61M 5/16831; A61M 5/31545; A61M 2005/208;
(Continued)

(56) References Cited

U.S. PATENT DOCUMENTS 4,282,872 A * 8/1981 Franetzki .............. A61M 5/172
604/67
5,366,346 A    11/1994 Danby
(Continued)

FOREIGN PATENT DOCUMENTS

JP    2003140802 A    5/2003
JP    2005057563 A    3/2005
(Continued)

OTHER PUBLICATIONS

Machine translation of JP 2013-206299 (Year: 2013).*
(Continued)

*Primary Examiner* — Patrick N Edouard
*Assistant Examiner* — Joseph P Fox
(74) *Attorney, Agent, or Firm* — Buchanan Ingersoll & Rooney PC

(57) ABSTRACT

A medical device is disclosed, which includes: an operation reception unit; a position acquisition unit capable of acquiring position information of a detection target that is in contact with or proximity to the operation reception unit, the position information being based on a position on the operation reception unit; and a control unit that identifies an operation input by the detection target based on a change in the acquired position information.

16 Claims, 15 Drawing Sheets

(51) Int. Cl.
    *A61M 5/315*     (2006.01)
    *G06F 3/0362*     (2013.01)
    *A61M 5/20*     (2006.01)

(52) U.S. Cl.
    CPC ..... *G06F 3/0362* (2013.01); *A61M 2005/208* (2013.01); *A61M 2205/17* (2013.01)

(58) Field of Classification Search
    CPC ........ A61M 2205/17; A61M 2205/505; A61M 5/16877; A61M 5/145; A61M 5/172; A61M 5/315; A61M 2005/14208; A61M 2205/3334; A61M 2205/52; G06F 3/0362
    See application file for complete search history.

(56) References Cited

U.S. PATENT DOCUMENTS

| | | | |
|---|---|---|---|
| 7,084,856 B2 * | 8/2006 | Huppi | G06F 3/03543 345/163 |
| 2003/0020687 A1 | 1/2003 | Sowden et al. | |
| 2010/0010647 A1 | 1/2010 | Schroeder et al. | |
| 2010/0265172 A1 * | 10/2010 | Sadahiro | G06F 3/03547 345/157 |
| 2014/0046296 A1 | 2/2014 | Clarke | |
| 2017/0000946 A1 | 1/2017 | Boyle et al. | |
| 2017/0053100 A1 | 2/2017 | Neftel | |
| 2017/0147105 A1 * | 5/2017 | Kwon | B60K 37/06 |

FOREIGN PATENT DOCUMENTS

| | | | | |
|---|---|---|---|---|
| JP | 2008253738 A | 10/2008 | | |
| JP | 2010088564 A | 4/2010 | | |
| JP | 2013084437 A | 5/2013 | | |
| JP | 2013171465 A | 9/2013 | | |
| JP | 2013206299 A | 10/2013 | | |
| JP | 2015182500 A | 10/2015 | | |
| JP | 2016-107321 A | 6/2016 | | |
| JP | 2017097855 A | 6/2017 | | |
| JP | 2017122983 A | 7/2017 | | |
| JP | 2017213057 A | 12/2017 | | |
| WO | WO-2007072316 A2 * | 6/2007 | ........... | G06F 3/0338 |

OTHER PUBLICATIONS

Office Action (The Second Office Action) dated Mar. 29, 2022, by the National Intellectual Property Administration in corresponding Chinese Patent Application No. 201880050427.9 and an English Translation of the Office Action. (20 pages).

The extended European Search Report dated Apr. 8, 2020, by the European Patent Office in corresponding European Patent Application No. 18863656.7-1122. (8 pages).

International Search Report (with English Translation) and Written Opinion issued in corresponding International Patent Application No. PCT/JP2018/031616, 12 pages (dated Nov. 20, 2018).

* cited by examiner

MEDICAL DEVICE

CROSS-REFERENCES TO RELATED APPLICATIONS

This application is a continuation of International Application No. PCT/JP2018/031616 filed on Aug. 27, 2018, which claims priority to Japanese Application No. 2017-191874 filed on Sep. 29, 2017, the entire content of both of which is incorporated herein by reference.

TECHNICAL FIELD

The present disclosure generally relates to a medical device, and more particularly to a medical device that receives operation input by an operator.

BACKGROUND DISCUSSION

Medical devices are known that include an input device that receives an operation input by operator, performs setting of a set value on the basis of the received input operation, and operates on the basis of the set value that has been set. An example of such a medical device includes a syringe pump on which a syringe storing a liquid such as a medical agent is placed, and that controls the speed at which a pusher of the placed syringe is pushed out in accordance with a set value set by an operator and thereby feeds the liquid into a living body of a patient while controlling the flow rate. There are cases where a medical device such as a syringe pump uses a rotating member such as a dial as an input device for setting a predetermined set value such as an administration rate, and the set value can be increased or decreased in accordance with the amount of rotation of the rotating member (for example, refer to Japanese Patent Application No. 2008-253738 A).

In medical devices using a rotating member as an input device, a gap is likely to be formed between the rotating member and a member such as a housing on which the rotating member is provided. Ingress of a liquid such as a highly viscous medical agent or other foreign substance into the gap between the rotating member and the member, for example, the housing, can make it difficult to rotate the rotating member, leading to deterioration in the operability of the input device.

SUMMARY

A medical device is disclosed, which is capable of suppressing deterioration of the operability of the medical device even with adhesion of a foreign substance such as a liquid.

A medical device in accordance with a first aspect of the present disclosure includes: an operation reception unit; a position acquisition unit configured to acquire position information of a detection target that is in contact with or proximity to the operation reception unit, the acquired position information being based on a position on the operation reception unit; and a control unit configured to identify an operation input by the detection target based on a change in the acquired position information.

In the medical device as an embodiment of the present disclosure, the control unit increases or decreases a predetermined set value on the basis of a change in the acquired position information in a circumferential direction around a predetermined center point on the operation reception unit.

In the medical device as an embodiment of the present disclosure, the control unit increases the set value in a case where the acquired position information changes in a first circumferential direction that is one direction of the circumferential direction and decreases the set value in a case where the acquired position information changes in a second circumferential direction that is the direction opposite to the first circumferential direction.

In the medical device as an embodiment of the present disclosure, the control unit increases or decreases the set value in accordance with a direction of an immediately preceding change in the acquired position information out of the first circumferential direction or the second circumferential direction in a case where the acquired position information has not changed for a predetermined time or more.

In the medical device as an embodiment of the present disclosure, the control unit increases or decreases the set value with an amount of change per unit time corresponding to an amount of change per unit time of the position information with an immediately preceding change in a case where the acquired position information has not changed for a predetermined time or more.

In the medical device as an embodiment of the present disclosure, the control unit is not to change the set value until subsequent acquired position information changes by a predetermined amount or more in a case where the direction of change in the acquired position information is switched from one of the first circumferential direction or the second circumferential direction, to the other direction.

In the medical device according to an embodiment of the present disclosure, the position acquisition unit includes a plurality of detection regions arranged in the circumferential direction, and acquires a detection region which the detection target is in contact with or in closest proximity to, out of the plurality of detection regions, as the position information of the detection target.

In the medical device as an embodiment of the present disclosure, the position acquisition unit includes a plurality of detection units arranged in the circumferential direction, and in a case where one detection unit out of the plurality of detection units detects a contact made by the detection target, the position acquisition unit acquires a stable detection region as a detection region of a position corresponding to the one detection unit, as the position information of the detection target, and in a case where two detection units adjacent in the circumferential direction out of the plurality of detection units simultaneously detect a contact made by the detection target, the position acquisition unit acquires a boundary detection region as a detection region between two stable detection regions corresponding to the two detection units, respectively, as the position information of the detection target.

The medical device as an embodiment of the present disclosure further includes a storage unit that stores one of the first circumferential direction or the second circumferential direction as a temporary storage direction, and the position acquisition unit acquires the position information at an acquisition timing occurring at a predetermined period, and in a case where latest position information acquired at a latest acquisition timing and immediately preceding position information acquired at an immediately preceding acquisition timing are two detection regions adjacent in the circumferential direction and in a case where the latest position information is the stable detection region, and when a moving direction being a direction of the latest position information with respect to the immediately preceding position information is the same as the temporary storage direction, the control unit increases or decreases the set value in accordance with the moving direction, and in a case where the latest position information is the boundary detection region, the control unit performs control to store the moving direction in the storage unit as the temporary storage direction.

In the medical device as an embodiment of the present disclosure, in a case where there is one detection region between the latest position information and the immediately preceding position information, and in a case where the latest position information is the stable detection region, the control unit increases or decreases the set value in accordance with the moving direction, and in a case where the latest position information is the boundary detection region, and when the moving direction is the same as the temporary storage direction, the control unit increases or decreases the set value in accordance with the moving direction.

In the medical device as an embodiment of the present disclosure, in a case where the detection region as the position information acquired at the latest acquisition timing is different from the detection region as the position information acquired at the immediately preceding acquisition timing, the control unit determines that the position information has changed in a direction in which a distance in the circumferential direction from the immediately preceding detection region to the latest detection region is shorter out of the first circumferential direction and the second circumferential direction, and increases or decreases the set value.

In the medical device as an embodiment of the present disclosure, in a case where the position acquisition unit has acquired the position information only within a predetermined time, the control unit changes a unit of increase/decrease of the set value based on a change in the position information in subsequent acquisition.

In the medical device as an embodiment of the present disclosure, in a case where the position acquisition unit cannot acquire the position information, the control unit would not use the previously acquired position information for increase/decrease of the set value.

In the medical device as an embodiment of the present disclosure, in a case where the position information has not changed for a predetermined time, the control unit stops increase/decrease of the set value until the amount of change in the position information exceeds a predetermined distance.

In the medical device as an embodiment of the present disclosure, in a case where the position information changes beyond a predetermined distance in one direction of the circumferential direction after the acquisition of the position information is started, the control unit increases or decreases the set value in accordance with the amount of change exceeding the predetermined distance.

In the medical device as an embodiment of the present disclosure, the operation reception unit includes a protrusion that protrudes at a position corresponding to the center point.

In the medical device as an embodiment of the present disclosure, the operation reception unit includes a circumferential wall protruding along a circumferential direction around the center point.

In the medical device as an embodiment of the present disclosure, the height of the circumferential wall is 15% to 45% with respect to a shortest distance between the circumferential wall and the protrusion.

In the medical device as an embodiment of the present disclosure, the operation reception unit includes a bottom and a circumferential wall formed with a circumferential surface extending along a circumferential direction around the center point and curved to have a recessed surface to be connected to the bottom, and a surface of at least one of the circumferential wall or the bottom has a partition at a position corresponding to each of boundary lines of the plurality of detection regions.

In the medical device as an embodiment of the present disclosure, the operation reception unit is a product integrally molded with a housing.

According to the medical device of the present disclosure, it is possible to suppress deterioration of operability even with adhesion of a foreign substance such as a liquid.

DETAILED DESCRIPTION

Figure 1:
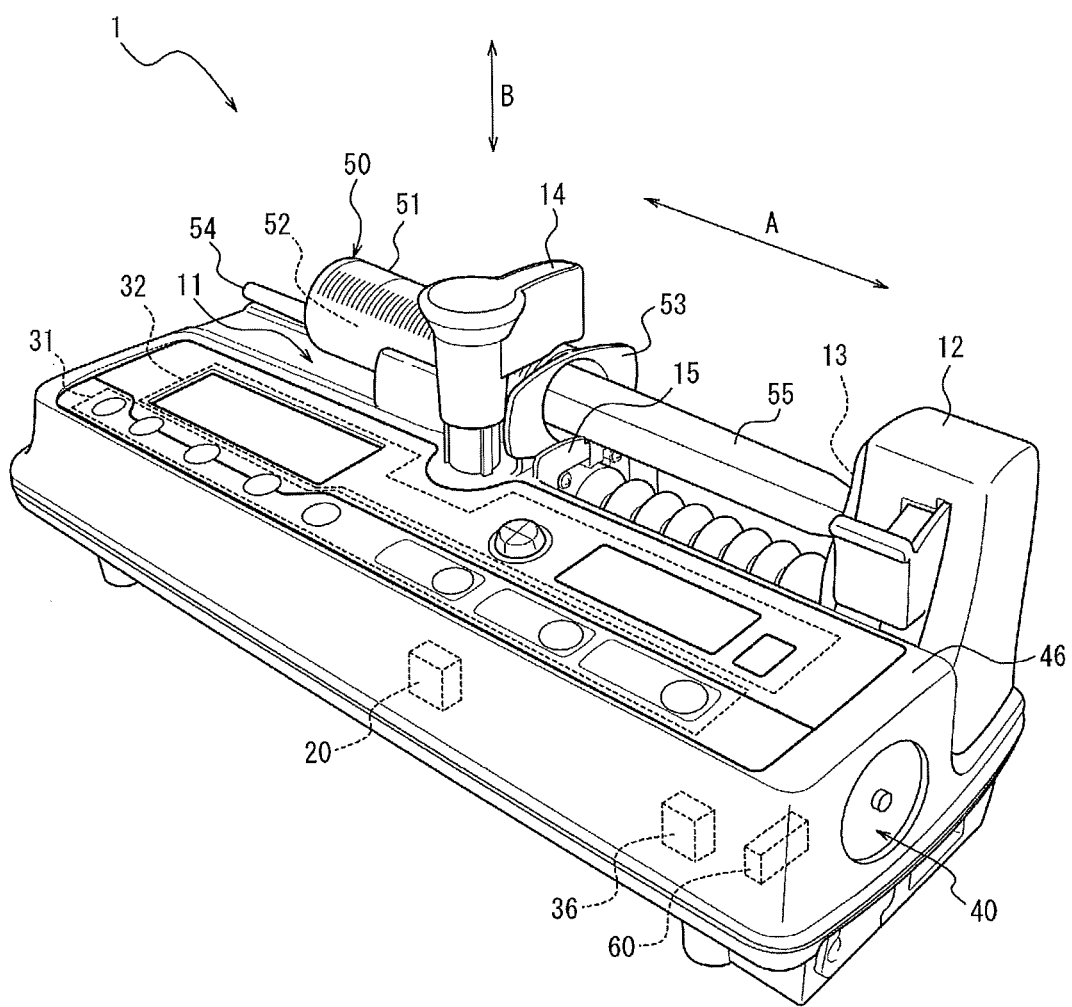
FIG. 1 is a perspective view of a syringe pump as a medical device according to an embodiment of the present disclosure.

Set forth below with reference to the accompanying drawings is a detailed description of embodiments of a medical device that receives operation input by operator representing examples of the inventive medical device that receives operation input by operator. In the drawings, common members are denoted by the same reference numerals.

Configuration of Syringe Pump

Figure 2:
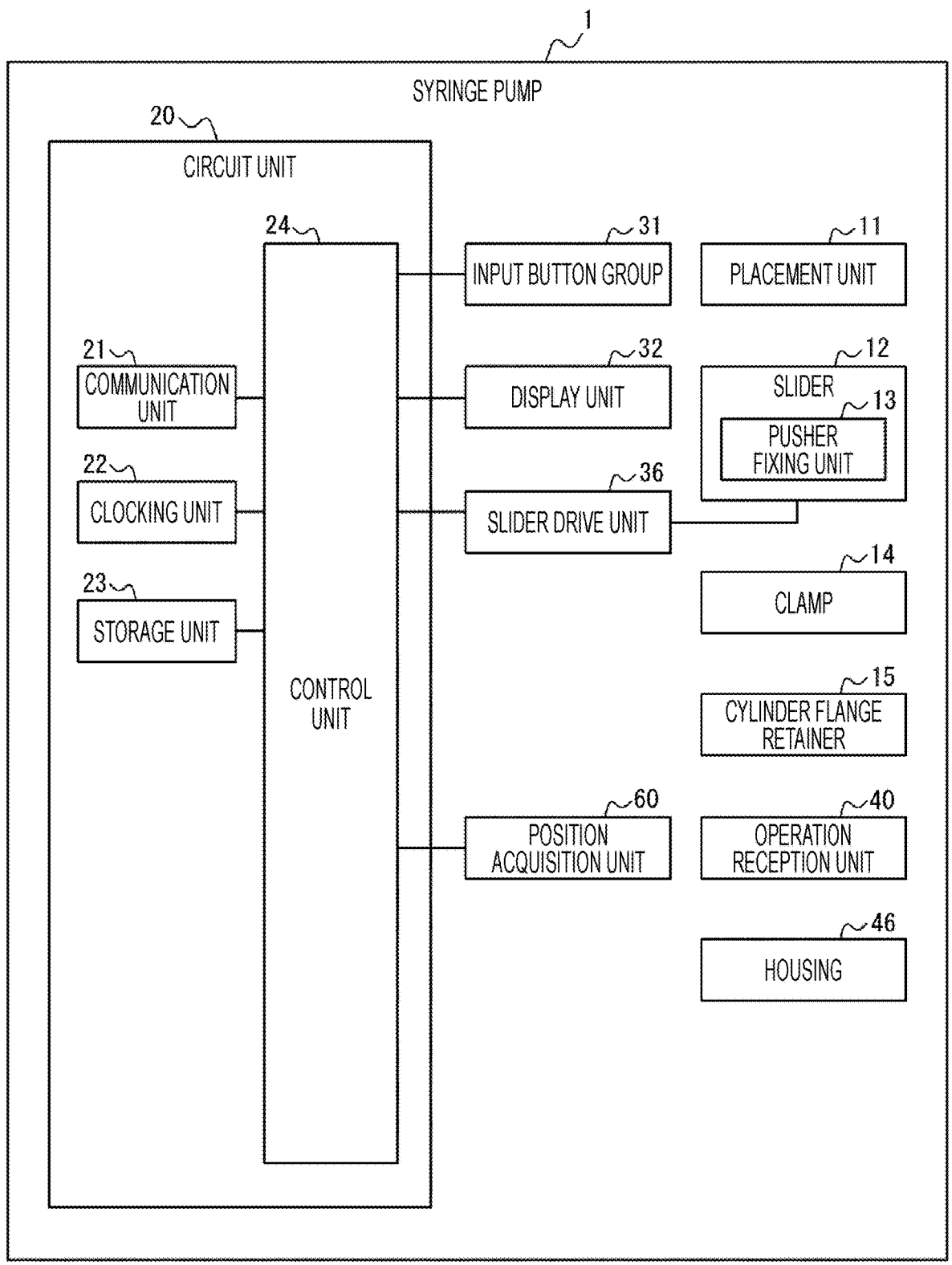
FIG. 2 is a block diagram illustrating a configuration of the syringe pump illustrated in FIG. 1.

FIG. 1 is a perspective view of a syringe pump 1 as a medical device according to an embodiment of the present disclosure. FIG. 1 illustrates the syringe pump 1 in a state where a syringe 50 is placed. As illustrated in FIG. 1, the syringe pump 1 can be implemented as a pump that feeds a liquid stored in a hollow portion 52 of the syringe 50. FIG. 2 is a block diagram illustrating a configuration of the syringe pump 1.

As illustrated in FIGS. 1 and 2, the syringe pump 1 includes a placement unit 11, a slider 12, a clamp 14, a cylinder flange retainer 15, a circuit unit 20, an input button group 31, a display unit 32, a slider drive unit 36, an operation reception unit 40, a housing 46, and a position acquisition unit 60.

As illustrated in FIG. 1, the syringe 50 can be placed on the placement unit 11. In accordance with an embodiment, the syringe 50 includes a cylinder 51 that has a cylindrical shape and includes the hollow portion 52; and a pusher 55 that is inserted into the hollow portion 52 from the proximal end side of the cylinder 51 and wherein the pusher 55 is movable within the hollow portion 52 along an extending direction A of the cylinder 51 (hereinafter simply referred to as the "extending direction A") while being in close contact, with no gap, with an inner circumferential surface of the cylinder 51 in the circumferential direction. The cylinder 51 has a cylinder flange 53 at the proximal end portion, and defines, at a distal end portion, an outlet hole 54 that allows communication between the hollow portion 52 and the outside. A flexible tube can be connected to the distal end portion of the cylinder 51. When the tube is connected to the distal end portion of the cylinder 51, the outlet hole 54 communicates with a flow path partitioned by the tube. A liquid such as a medical agent can be stored in the hollow portion 52 of the syringe 50. Hereinafter, in the extending direction A, the distal end side of the cylinder 51 will be referred to as "a distal end side in the extending direction A", and the proximal end side of the cylinder 51 as "a proximal end side in the extending direction A".

As illustrated in FIG. 1, the cylinder 51 of the syringe 50 can be placed on the placement unit 11. As illustrated in FIG. 1, the cylinder flange retainer 15 stores a part of the cylinder flange 53 after the cylinder 51 of the syringe 50 is placed on the placement unit 11, which fixes the position of the cylinder 51 with respect to the syringe pump 1.

As illustrated in FIG. 1, the slider 12 includes a pusher fixing part 13. The slider 12 is movable so as to engage with the pusher 55 of the syringe 50 placed on the placement unit 11. Specifically, the slider 12 is movable in the extending direction A at a position closer to the proximal end in the extending direction A than the pusher 55 of the syringe 50 placed on the placement unit 11. The slider 12 causes the pusher fixing part 13 to fix the pusher 55 of the syringe 50 placed on the placement unit 11. In a state where the pusher 55 is fixed to the slider 12 by the pusher fixing part 13, the pusher 55 moves integrally with the slider 12 in accordance with the movement of the slider 12 in the extending direction A. At this time, the cylinder 51 placed on the placement unit 11 is fixed by the cylinder flange retainer 15 in the extending direction A with respect to the syringe pump 1. Therefore, when the slider 12 moves to the distal end side of the syringe 50, the pusher 55 moves to the distal end side with respect to the cylinder 51, so as to discharge the liquid stored in the hollow portion 52 of cylinder 51 from the outlet hole 54, which makes it possible to feed the liquid stored in the hollow portion 52 into the living body through the flow path defined by the tube connectable to the distal end portion of the cylinder 51.

As illustrated in FIG. 1, the clamp 14 is movable in a direction B orthogonal to the extending direction A, so as be able to fix the cylinder 51 of the placed syringe 50 sandwiched between the placement unit 11 and the clamp 14. In accordance with an embodiment, fixing the cylinder 51 with the clamp 14 makes it rather difficult for a part of the cylinder flange 53 to be detached from the cylinder flange retainer 15, and so that the cylinder 51 can be relatively firmly fixed to the syringe pump 1.

As illustrated in FIG. 2, the circuit unit 20 includes a communication unit 21, a clocking unit 22, a storage unit 23, and a control unit 24.

The communication unit 21 includes an interface that transmits and receives information to and from an information processing apparatus such as an external computer by wireless or wired communication.

The clocking unit 22 measures and keeps time. In accordance with an embodiment, the clocking unit 22 can be implemented by a Real Time Clock (RTC), for example. The clocking unit 22 may be implemented as a function of the control unit 24.

The storage unit 23 includes a storage device, for example, and stores various information and programs. Specifically, the storage unit 23 stores a program for executing a set value increase/decrease process, various input support processes, or the like, to be executed by the control unit 24. The storage unit 23 stores information including a predetermined set value such as the flow rate and dose of the liquid fed by the syringe pump 1 (hereinafter simply referred to as "set values"), a control program for driving the slider drive unit 36 for feeding liquid on the basis of the set value, or the like. The storage unit 23 stores information regarding one of the first circumferential direction or the second circumferential direction, as a temporary storage direction. Details of the temporary storage direction stored in the storage unit 23 will be described below.

The control unit 24 includes, for example, a processor that implements a predetermined function by reading predetermined information and programs out of various information and programs stored in the storage unit 23, for example, and controls the overall operation of the syringe pump 1. As will be described below, the control unit 24 identifies operation input from the operation reception unit 40 by a detection target such as an operator's fingertip. Specifically, the control unit 24 reads predetermined information and a program stored in the storage unit 23, and executes processes such as a set value increase/decrease process and various input support processes. The control unit 24 transmits/receives information to/from an external information processing apparatus via the communication unit 21. The control unit 24 executes various processes on the basis of the information input from the input button group 31 and the position acquisition unit 60, and outputs information associated with the execution of the various processes from the display unit 32.

As illustrated in FIG. 1, the input button group 31 includes various operation buttons that are arranged on a surface of the housing 46 and can receive operation input by operator. The input button group 31 can include, for example, a power button for switching on/off of the operation power of the syringe pump 1, a start button for starting liquid feeding from the syringe pump 1, and a stop button for stopping liquid feeding from the syringe pump 1. The input button group 31 outputs the input information to the control unit 24.

As illustrated in FIG. 1, the display unit 32 includes a display device such as a liquid crystal display or an organic electroluminescence (EL) display, for example. On the basis of a signal from the control unit 24, the display unit 32 displays a set value or an actual value of the flow rate of the liquid to be fed, a set value or an actual value of the dose of the liquid to be fed, various alarm information, or the like.

The slider drive unit 36 includes a motor, for example, and moves the slider 12 in the extending direction A (refer to FIG. 1) on the basis of a signal from the control unit 24.

As illustrated in FIG. 1, the operation reception unit 40 is arranged to be at least partly exposed to the outside of the syringe pump 1. Details of the operation reception unit 40 will be described below.

In accordance with an embodiment, the position acquisition unit 60 can acquire position information based on the position on the operation reception unit 40 of a detection target such as an operator's fingertip that comes in contact with or in proximity to the operation reception unit 40. The position acquisition unit 60 acquires position information over time. Specifically, the position acquisition unit 60 acquires position information at a predetermined acquisition timing. The predetermined acquisition timing occurs at a predetermined period, for example. The predetermined acquisition timing, for example, occurs every 10 milliseconds. In this case, the position acquisition unit 60 acquires position information every 10 milliseconds. However, the predetermined period is not limited to 10 milliseconds. The predetermined period may be appropriately determined in accordance with the usage or specification of the operation reception unit 40. However, the position acquisition unit 60 preferably acquires position information every 5 milliseconds to 100 milliseconds, and more preferably acquires position information every 5 milliseconds to 50 milliseconds. Setting the time interval at which the position acquisition unit 60 acquires position information to be an upper limit of the above range of 50 milliseconds or less can make it possible to reduce the possibility of erroneous recognition by the control unit 24 that the detection target has rotated reversely in a case where the position of the detection target is quickly changed. The position acquisition unit 60 outputs the acquired position information to the control unit 24.

An example of the position acquisition unit 60 is an electric field type position detection sensor that generates an electric field around the operation reception unit 40 and detects a disturbance of the electric field generated by the detection target coming in proximity to the operation reception unit 40, and thereby can acquire the position information of the detection target. Another example of the position acquisition unit 60 is a capacitance type position detection sensor that detects a change in capacitance generate by the detection target coming in contact with the surface of the operation reception unit 40, and thereby can acquire the position information of the detection target. In a case where the position acquisition unit 60 is the above-described electric field type position detection sensor, for example, the position information of the detection target can be acquired even in a case where the operator wears rubber gloves or the like and the operator's finger does not directly touch the operation reception unit 40.

Figure 3:
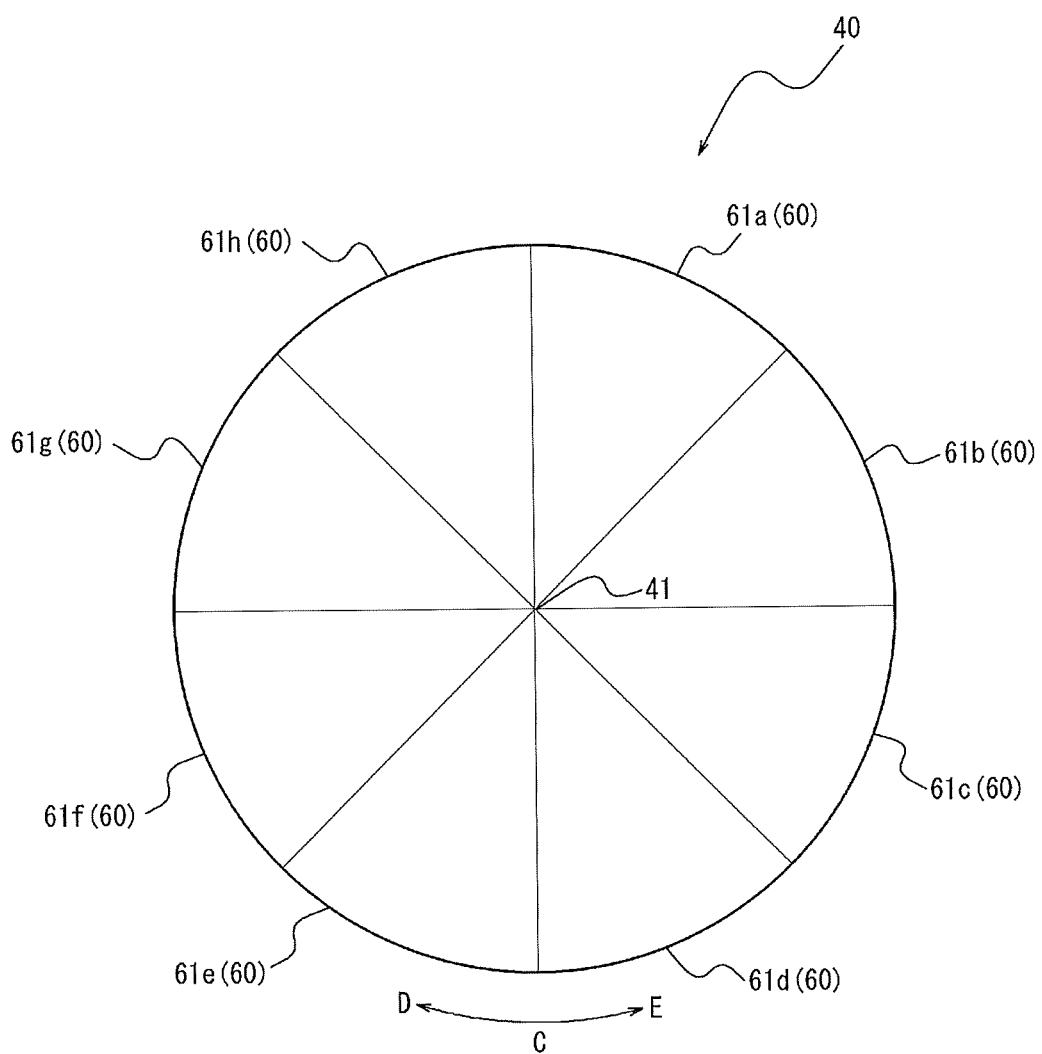
FIG. 3 is a view illustrating a detection region of a position acquisition unit provided in the syringe pump illustrated in FIG. 1.

FIG. 3 is a diagram illustrating an arrangement of detection regions as position information that can be acquired by the position acquisition unit 60. As illustrated in FIG. 3, the position acquisition unit 60 of the present embodiment includes a plurality of detection regions, for example, eight fan-shaped (i.e., pie-shaped) detection regions 61a to 61h, arranged without gaps in the circumferential direction C around the center point 41 on the operation reception unit 40.

In accordance with an embodiment, the position acquisition unit 60 acquires, as the position information of the detection target, a detection region that is in contact with or in closest proximity to the detection target from the plurality of detection regions 61a to 61h. Specifically, in a case where the position acquisition unit 60 is implemented as an electric field type position detection sensor, for example, the position acquisition unit 60 acquires information indicating the position of the detection target in a three-dimensional space, and acquires a detection region which the position is in closest proximity to, as the position information of the detection target. In a case where the position acquisition unit 60 is implemented as a capacitance type position detection sensor, for example, each of a plurality of detection regions includes a detection unit such as a touch pad capable of detecting the contact made by the detection target, and acquires the detection region in which contact is detected as the position information of the detection target. The position acquisition unit 60 outputs detection region information as the acquired position information to the control unit 24. Hereinafter, the position information of the detection target acquired by the position acquisition unit 60 will be referred to as "acquired position information", and the detection region acquired as position information of the detection target by the position acquisition unit 60 will be referred to as "acquired detection region".

As described above, the syringe pump 1 as the medical device of the present embodiment includes: the operation reception unit 40; the position acquisition unit 60 capable of acquiring position information of the detection target that comes in contact with or in proximity to the operation reception unit 40 based on a position on the operation reception unit 40; and the control unit 24 that identifies operation input by a detection target based on a change in position information acquired by the position acquisition unit 60. With this configuration, the syringe pump 1 does not need to include a rotating member that physically rotates as an input device, making it possible to suppress deterioration of operability even with adhesion of a foreign substance such as a liquid. Furthermore, since the syringe pump 1 does not need to include a rotating member, the syringe pump 1 can have a configuration with a relatively small gap, which makes it possible to improve the cleanability of the syringe pump 1.

Syringe Pump Processing

Figure 4:
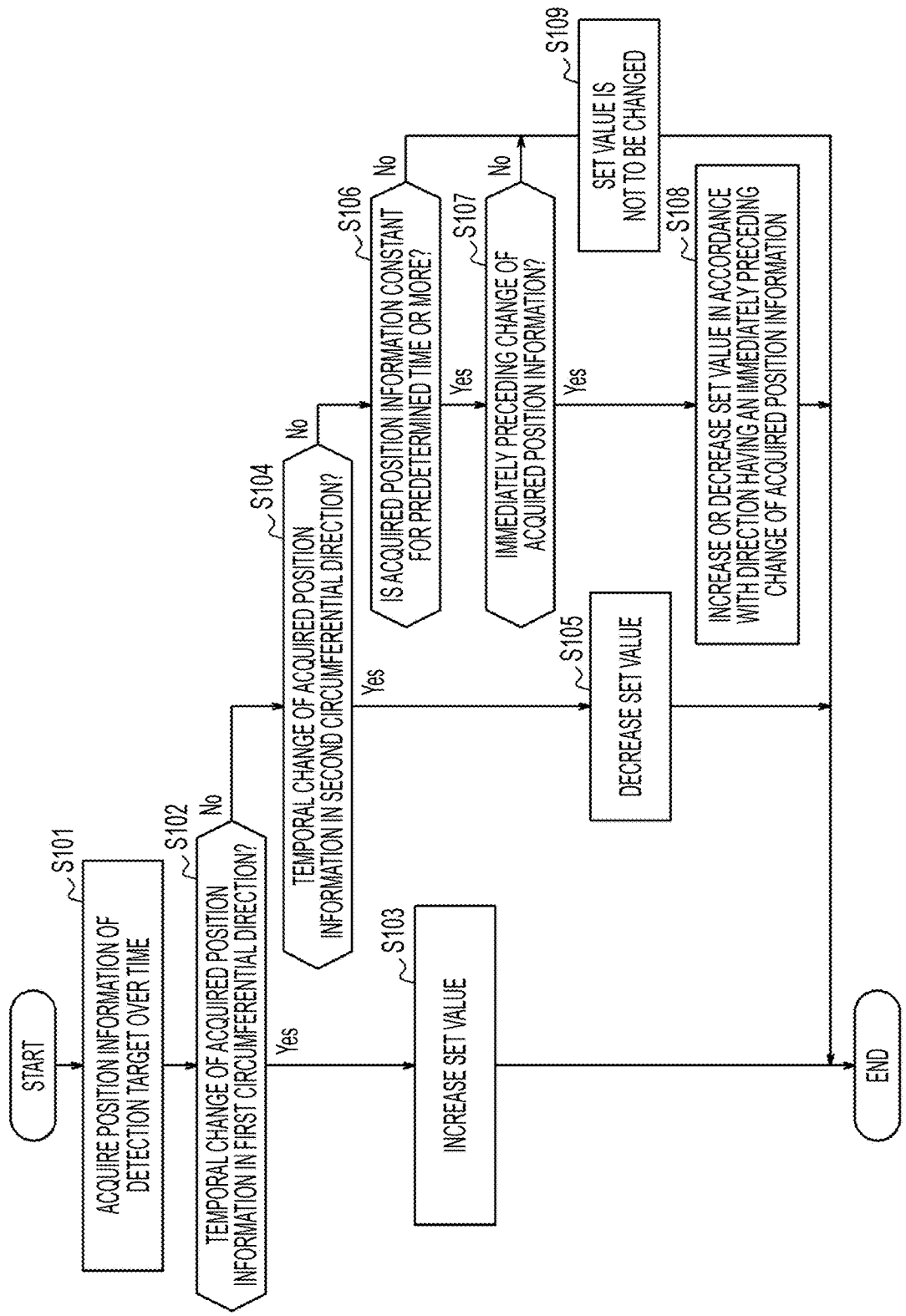
FIG. 4 is a flowchart illustrating a set value increase/decrease process executed by the syringe pump illustrated in FIG. 1.

FIG. 4 is a flowchart illustrating the set value increase/decrease process executed by the syringe pump 1. As illustrated in FIG. 4, first, the syringe pump 1 uses the position acquisition unit 60 to acquire position information of a detection target over time (step S101). Specifically, the position acquisition unit 60 acquires position information of the detection target for each and every predetermined unit of time, for example, every 50 milliseconds, and outputs the acquired position information to the control unit 24.

Thereafter, the control unit 24 identifies the operation input by the detection target on the basis of the temporal change (i.e., a change with time) of the acquired position information. For example, the control unit 24 increases or decreases the set value on the basis of a temporal change in the circumferential direction C (refer to FIG. 3), of the acquired detection region. Specifically, the control unit 24 performs the following steps S102 to S107.

The control unit 24 determines whether the acquired position information has a temporal change in the first circumferential direction D (refer to FIG. 3), which is one direction of the circumferential direction C (step S102). Specifically, the control unit 24 determines whether the acquired detection region has a temporal change in the first circumferential direction D between two detection regions adjacent to each other, that is, whether the acquired detection region has a temporal change from the detection region 61*a* to the detection region 61*b*.

In a case where the control unit 24 determines that the acquired position information has a temporal change in the first circumferential direction D (Yes in step S102), the control unit 24 increases the set value (step S103). In contrast, in a case where the control unit 24 determines that the acquired position information has no temporal change in the first circumferential direction D (No in step S102), the control unit 24 proceeds to the process of step S104.

The control unit 24 determines whether the acquired position information has a temporal change in a second circumferential direction E (refer to FIG. 3), which is the other side in the circumferential direction C, that is, a direction opposite to the first circumferential direction D (step S104). Specifically, the control unit 24 determines whether the acquired detection region has a temporal change in the second circumferential direction E between two detection regions adjacent to each other, that is, whether the acquired detection region has a temporal change from the detection region 61*a* to the detection region 61*h*, for example.

In a case where the control unit 24 determines that the acquired position information has a temporal change in the second circumferential direction E (Yes in step S104), the control unit 24 decreases the set value (step S105). In contrast, in a case where the control unit 24 determines that the acquired position information has no temporal change in the second circumferential direction E (No in step S104), the control unit 24 proceeds to the process of step S106.

The control unit 24 determines whether the acquired position information is constant for a predetermined time or longer (step S106). The predetermined time used in the process of step S106 is stored in advance in the storage unit 23 and can be, for example, one second.

In a case where the control unit 24 determines that the acquired position information is constant for a predetermined time or longer (Yes in step S106), the control unit 24 determines whether the acquired position information has an immediately preceding change (step S107). In other words, the control unit 24 determines, in the process of step S107, whether the acquired position information until an immediately preceding time of the initially acquired position information used as the basis for the determination in step S106 has changed. At this time, for example, in a case where there is a period in which the position acquisition unit 60 is incapable of acquiring the position information of the detection target because the detection target is once separated from the operation reception unit 40, the previously acquired position information has been reset by a second input support process described below. Therefore, in this case, only the position information of the detection target continuously acquired again by the position acquisition unit 60 will be a determination target in the process of step S107.

In a case where the control unit 24 determines that the acquired position information has an immediately preceding change (Yes in step S107), the control unit 24 increases or decreases the set value in accordance with the direction having an immediately preceding temporal change of the acquired position information from the first circumferential direction D and the second circumferential direction E (step S108). Specifically, the control unit 24 increases the set value in a case where the direction having an immediately preceding temporal change of the acquired position information is the first circumferential direction D. In contrast, the control unit 24 decreases the set value in a case where the direction having an immediately preceding temporal change of the acquired position information is the second circumferential direction E. Thereafter, the control unit 24 continues increase/decrease of the set value during a period when the acquired position information is constant.

In a case where the control unit 24 determines that the acquired position information is not constant for a predetermined time or longer (No in step S106), or determines that the acquired position information has no immediately preceding change (No in step S107), the control unit 24 will not change the set value (step S109).

As described above, in a case where the acquired position information is constant for a predetermined time or longer and the acquired position information has an immediately preceding change, the syringe pump 1 increases or decreases the set value in accordance with the direction in which the acquired position information has an immediately preceding temporal change. Therefore, the operator can continue increase/decrease of the set value in accordance with the direction of an immediately preceding change of the detection target without a need to continuously move the detection target.

In the process of step S108, the control unit 24 may increase or decrease the set value with a constant amount of change per unit time. With this configuration, the operator can estimate the remaining time before the set value reaches the target value by checking the set value that changes at a constant speed on the display unit 32, facilitating the setting of the set value to the target value.

In the process of step S108, the control unit 24 may increase or decrease the set value by the amount of change per unit time corresponding to the amount of change per unit time of the position information having an immediately preceding change. In other words, the control unit 24 may determine the amount of change in the set value per unit time in accordance with the amount of change per unit time in the position information having an immediately preceding change. Specifically, the control unit 24 may perform control so that the greater the amount of change per unit time of the position information having an immediately preceding change, the greater the amount of change in the set value per unit time. In this manner, since the syringe pump 1 determines the speed of change in the set value in accordance with the change speed of the position information having an immediately preceding change, the set value can be changed at a speed corresponding to the operator's immediately preceding operation.

Figure 5:
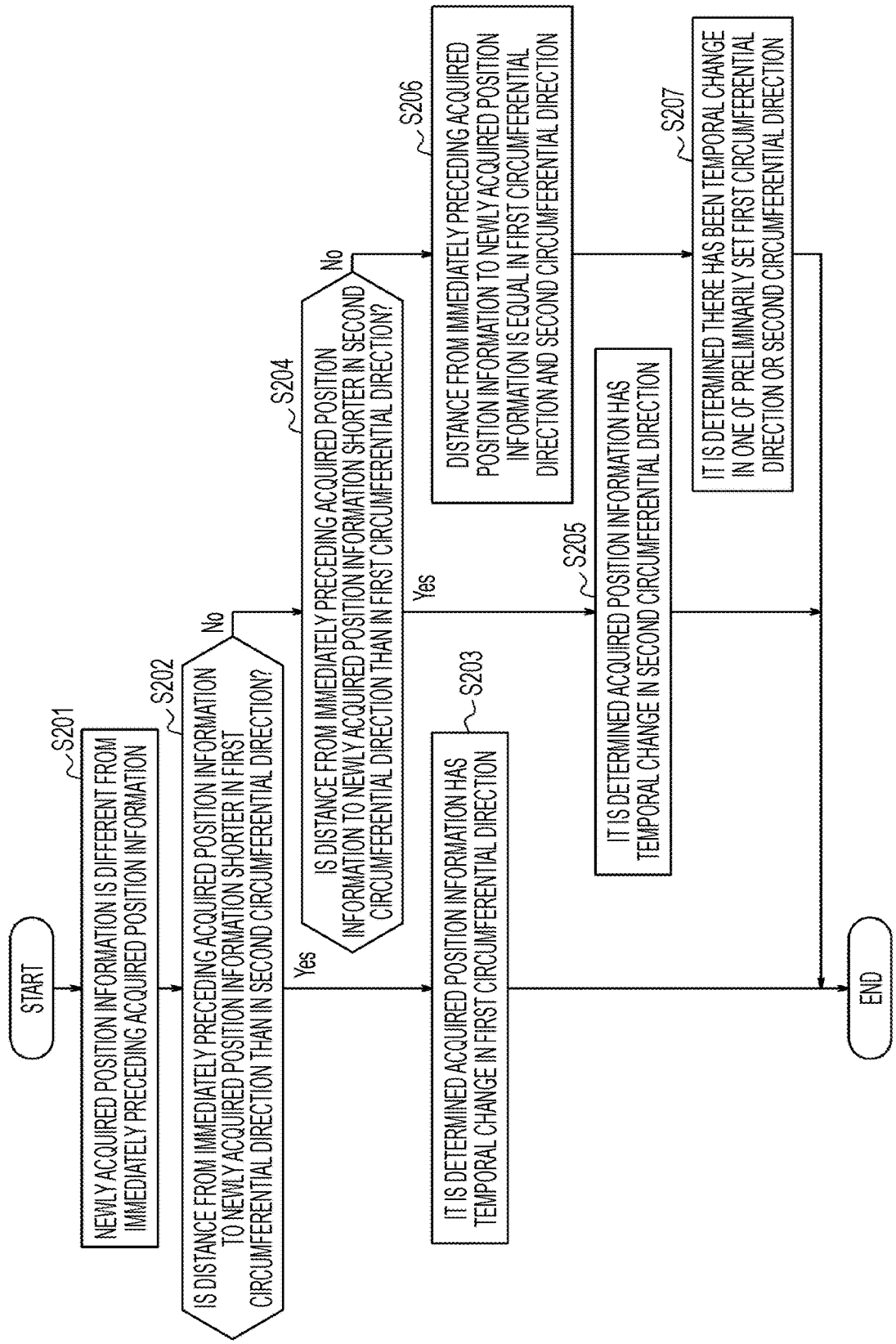
FIG. 5 is a flowchart illustrating a modification of part of the set value increase/decrease process illustrated in FIG. 4.

In the set value increase/decrease process illustrated in FIG. 4, the process of step S102 and the process of step S104 can also be executed as follows. FIG. 5 is a flowchart illustrating a modification of the process of step S102 and the process of step S104 as a part of the set value increase/decrease process.

As illustrated in FIG. 5, in a case where the newly acquired position information is different from the immediately preceding acquired position information (step S201), the control unit 24 determines whether a distance in the first circumferential direction D from the immediately preceding acquired position information to the newly acquired position information is shorter than a distance in the second circumferential direction E (step S202). Specifically, in a case where the acquired detection region as the newly acquired position information is different from the acquired detection region as the immediately preceding acquired position information, the control unit 24 determines whether a distance in the first circumferential direction D from the immediately preceding acquired detection region to the newly acquired detection region is shorter than a distance in the second circumferential direction E.

In a case where the control unit 24 determines that the distance in the first circumferential direction D from the immediately preceding acquired position information to the newly acquired position information is shorter than (i.e., less than) the distance in the second circumferential direction E (Yes in step S202), the control unit 24 determines that the acquired position information has a temporal change in the first circumferential direction D (step S203), and increases the set value (step S103 in FIG. 4). In contrast, in a case where the control unit 24 determines that the distance in the first circumferential direction D from the immediately preceding acquired position information to the newly acquired position information is the distance or greater in the second circumferential direction E (No in step S202), the process proceeds to step S204. For example, in a case where the acquired detection region as the immediately preceding acquired position information is the detection region 61a (refer to FIG. 3), and the acquired detection region as the newly acquired position information is the detection region 61d (refer to FIG. 3), the distance in the first circumferential direction D from the detection region 61a to the detection region 61d is shorter than the distance in the second circumferential direction E. Therefore, the control unit 24 determines that the acquired detection region as the acquired position information has a temporal change in the first circumferential direction D, and increases the set value.

In a case where the control unit 24 determines that the distance in the second circumferential direction E from the immediately preceding acquired position information to the newly acquired position information is shorter than the distance in the first circumferential direction D (Yes in step S204), the control unit 24 determines that the acquired position information has a temporal change in the second circumferential direction E (step S205), and decreases the set value (step S105 in FIG. 4). For example, in a case where the acquired detection region as the immediately preceding acquired position information is the detection region 61a (refer to FIG. 3), and the acquired detection region as the newly acquired position information is the detection region 61f (refer to FIG. 3), the distance in the second circumferential direction E from the detection region 61a to the detection region 61f is shorter than the distance in the first circumferential direction D. Therefore, the control unit 24 determines that the acquired detection region as the acquired position information has a temporal change in the second circumferential direction E, and decreases the set value.

In a case where the distance in the first circumferential direction D from the immediately preceding acquired position information to the newly acquired position information is the distance in the second circumferential direction E or greater (No in step S202), and in a case where the distance in the second circumferential direction E is the distance in the first circumferential direction D or greater (No in step S204), it is determined that the distance in the first circumferential direction D and the distance in the second circumferential direction E from the immediately preceding acquired position information to the newly acquired position information are equal (step S206). At this time, the control unit 24 determines that the acquired position information has a temporal change in either the first circumferential direction D or the second circumferential direction E set in advance (step S207), and increases or decreases the set value (step S103 or S105 in FIG. 4).

As described above, in a case where the acquired detection region as the newly acquired position information is different from the acquired detection region as the immediately preceding acquired position information, the syringe pump 1 as the medical device of the present embodiment determines that the position information has a temporal change in a direction having a shorter distance from the immediately preceding acquired detection region to the newly acquired detection region in the circumferential direction C, from the first circumferential direction D and the second circumferential direction E, and can increase or decrease the set value. Accordingly, even in a case where there is a detection region that cannot be acquired as an acquired detection region due to the movement of the detection target at a predetermined speed or more in the first circumferential direction D or the second circumferential direction E, the syringe pump 1 can determine that the acquired detection region has a temporal change in one of the first circumferential direction D or the second circumferential direction E and can increase or decrease the set value.

Figure 6:
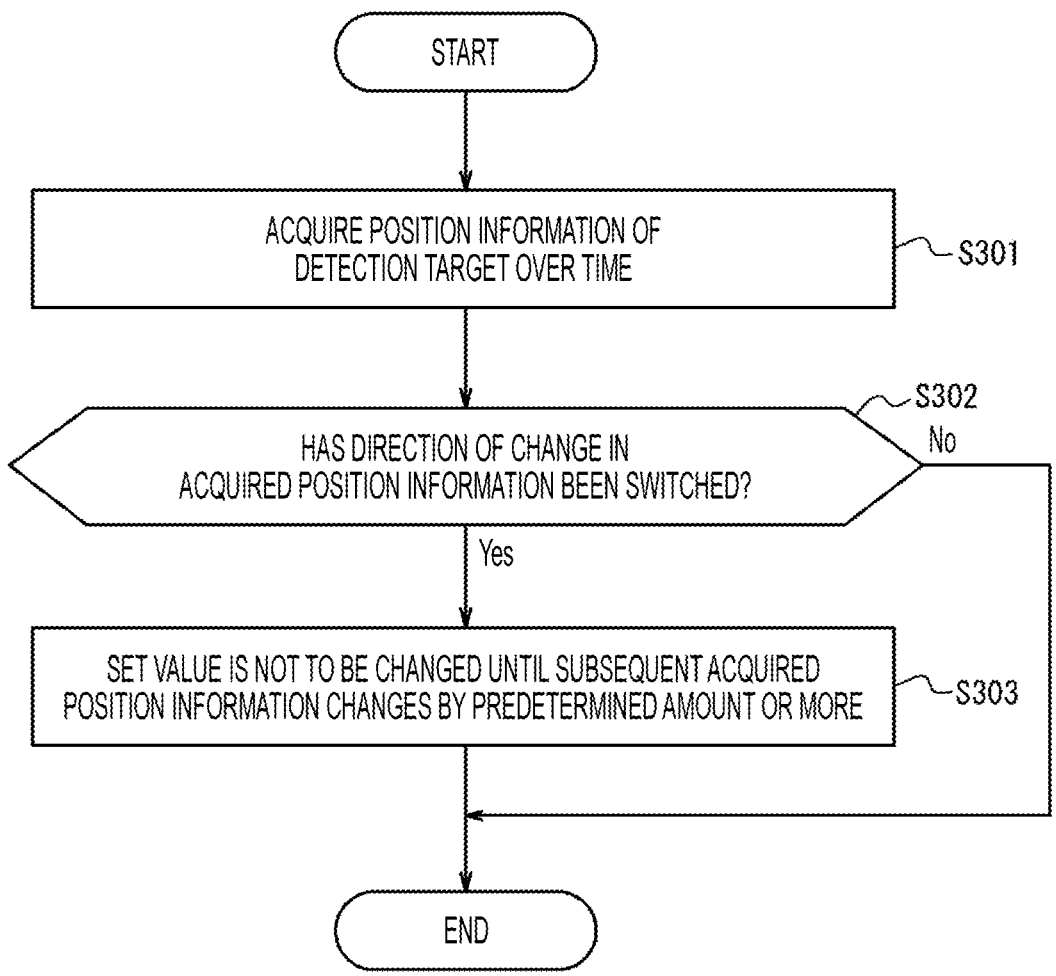
FIG. 6 is a flowchart illustrating a first input support process executed by the syringe pump illustrated in FIG. 1.

In accordance with an embodiment, the syringe pump 1 can execute the following input support processes in parallel with the set value increase/decrease process illustrated in FIGS. 4 and 5. FIG. 6 is a flowchart illustrating a first input support process executed by the syringe pump 1.

As illustrated in FIG. 6, the syringe pump 1 uses the position acquisition unit 60 to acquire position information of the detection target over time (step S301). The process of step S301 is similar to the process of step S101 (refer to FIG. 4).

The control unit 24 determines whether the direction of the temporal change of the acquired position information has been switched from one of the first circumferential direction D or the second circumferential direction E to the other (step S302).

In a case where the control unit 24 determines that the direction of the temporal change of the acquired position information has been switched (Yes in step S302), the control unit 24 will not change the set value until there is a subsequent acquired position information change by a predetermined amount or more (step S303). In contrast, in a case where the control unit 24 determines that the direction of the temporal change of the acquired position information has not been switched (No in step S302), the control unit 24 returns to the normal set value increase/decrease process. Specifically, in a case where the direction of the temporal change of the acquired detection region as the acquired position information has been switched, the control unit 24 will not increase or decrease the set value until the detection region in subsequent acquisition moves by a predetermined number of regions, for example, two, in the direction after the switching of directions.

As described above, even in a case where the syringe pump 1 as the medical device of the present embodiment has detected movement of the detection target in a reverse direction when the detection target is moving in one of the first circumferential direction D or the second circumferential direction E, the syringe pump 1 would not reflect the movement to the increase/decrease of the set value when the movement is less than a predetermined distance. Accordingly, it is possible to suppress the occurrence of false detection.

Figure 7:
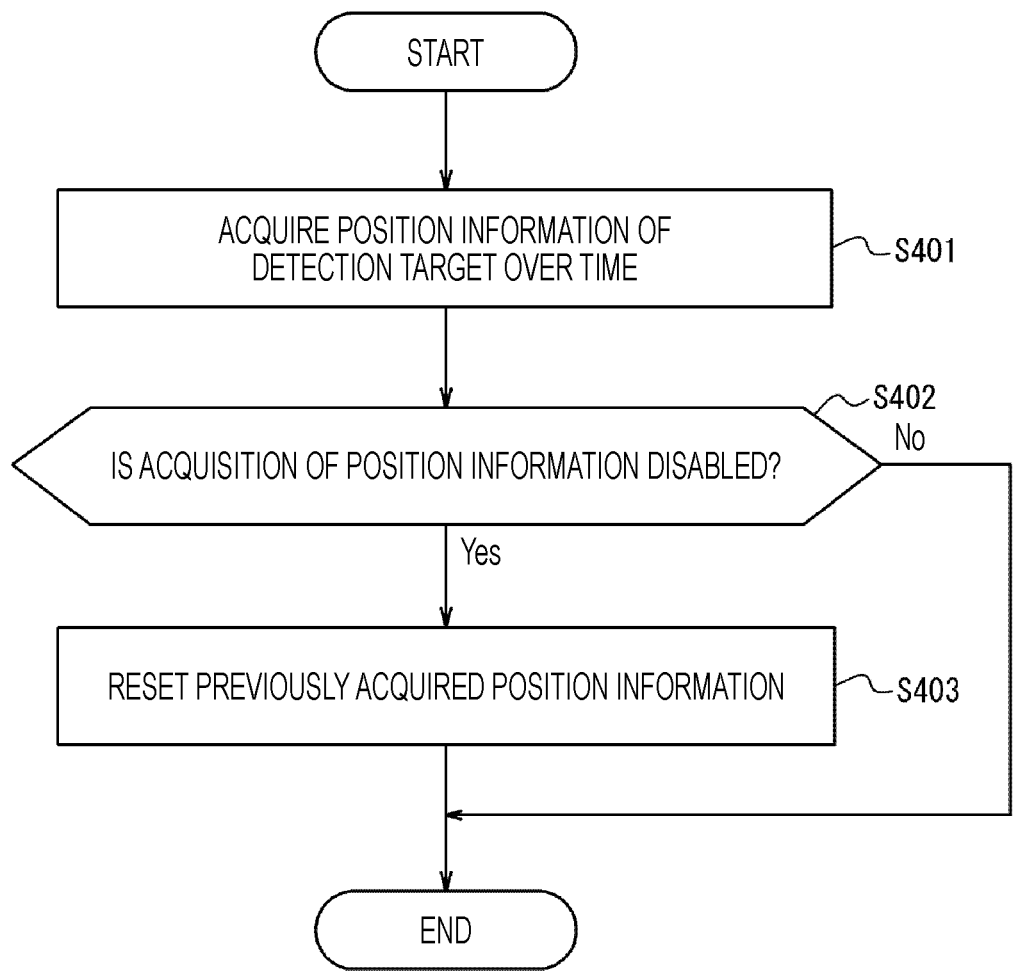
FIG. 7 is a flowchart illustrating a second input support process executed by the syringe pump illustrated in FIG. 1.

FIG. 7 is a flowchart illustrating a second input support process executed by the syringe pump 1. As illustrated in FIG. 7, the syringe pump 1 uses the position acquisition unit 60 to acquire position information of the detection target over time (step S401). The process of step S401 is similar to the process of step S101 (refer to FIG. 4).

In accordance with an embodiment, the control unit 24 determines whether acquisition of position information is disabled, that is, whether position information cannot be acquired by the position acquisition unit 60 (step S402).

In a case where the control unit 24 determines that acquisition of the position information is disabled (Yes in step S402), the control unit 24 resets the previously acquired position information, that is, will not use the previously acquired position information for subsequent increase/decrease of the set value (step S403). In contrast, in a case where the control unit 24 does not determine that acquisition of the position information is disabled (No in step S402), the control unit 24 returns to the normal set value increase/decrease process.

As described above, in a case where the acquisition of the position information is disabled, the syringe pump 1 as the medical device of the present embodiment resets the previously acquired position information and will not use the information for subsequent increase/decrease of the set value. Therefore, in a case where the position information of the detection target is acquired at a different position after the detection target is separated from the operation reception unit 40, the syringe pump 1 can increase or decrease the set value in accordance with the movement of the newly acquired position information.

Figure 8:
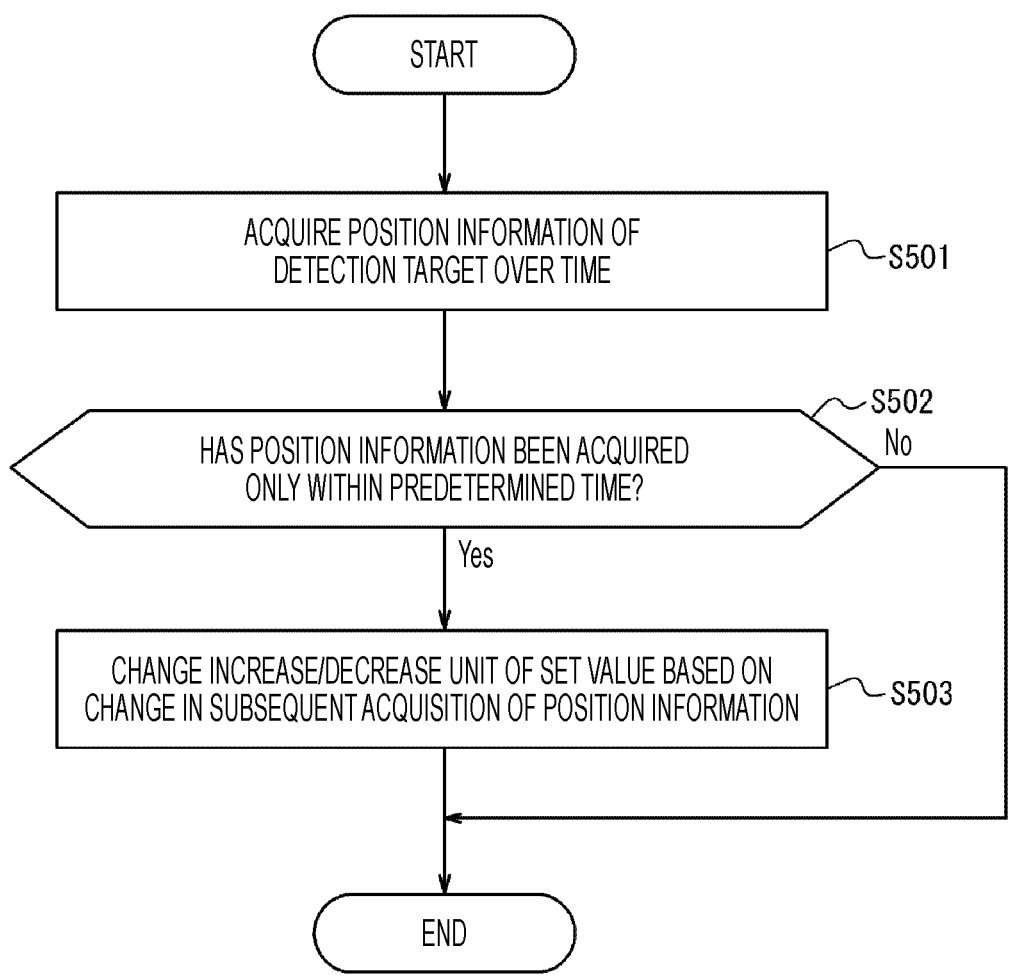
FIG. 8 is a flowchart illustrating a third input support process executed by the syringe pump illustrated in FIG. 1.

FIG. 8 is a flowchart illustrating a third input support process executed by the syringe pump 1. As illustrated in FIG. 8, the syringe pump 1 uses the position acquisition unit 60 to acquire position information of the detection target over time (step S501). The process of step S501 is similar to the process of step S101 (refer to FIG. 4).

In accordance with an embodiment, the control unit 24 determines whether the position acquisition unit 60 has acquired the position information only within a predetermined time (step S502). Specifically, the control unit 24 determines whether the time of continuous acquisition of the position information by the position acquisition unit 60 over time has ended within a predetermined time.

In a case where the control unit 24 determines that the position acquisition unit 60 has acquired the position information only within a predetermined time (Yes in step S502), the control unit 24 changes the unit of increase/decrease of the set value based on the temporal change of the position information subsequently acquired by the position acquisition unit 60 (step S503). Specifically, the change in the increase/decrease unit of the set value may be a change in the digit of the set value that increases or decreases in accordance with the temporal change of the acquired position information, for example, a change from the first digit to the tenth digit.

As described above, the syringe pump 1 as the medical device of the present embodiment receives simple operation such as operator's tap operation on the operation reception unit 40 with a detection target such as a fingertip, for example, making it possible to change the unit of subsequent increase/decrease of the set values.

In accordance with an embodiment, the position acquisition unit 60 is implemented with a capacitance type position detection sensor, etc., and it is possible to detect two adjacent detection regions simultaneously when detecting a contact made by a detection target using the position detection sensor or the like. In that case, the control unit 24 may perform the process assuming that a virtual detection region located between the two acquired detection regions has been acquired. For example, it is possible to acquire eight virtual detection regions between each of the eight detection regions 61a to 61h illustrated in FIG. 3. This makes it possible to detect the position information of the detection target with higher definition.

Figure 9:
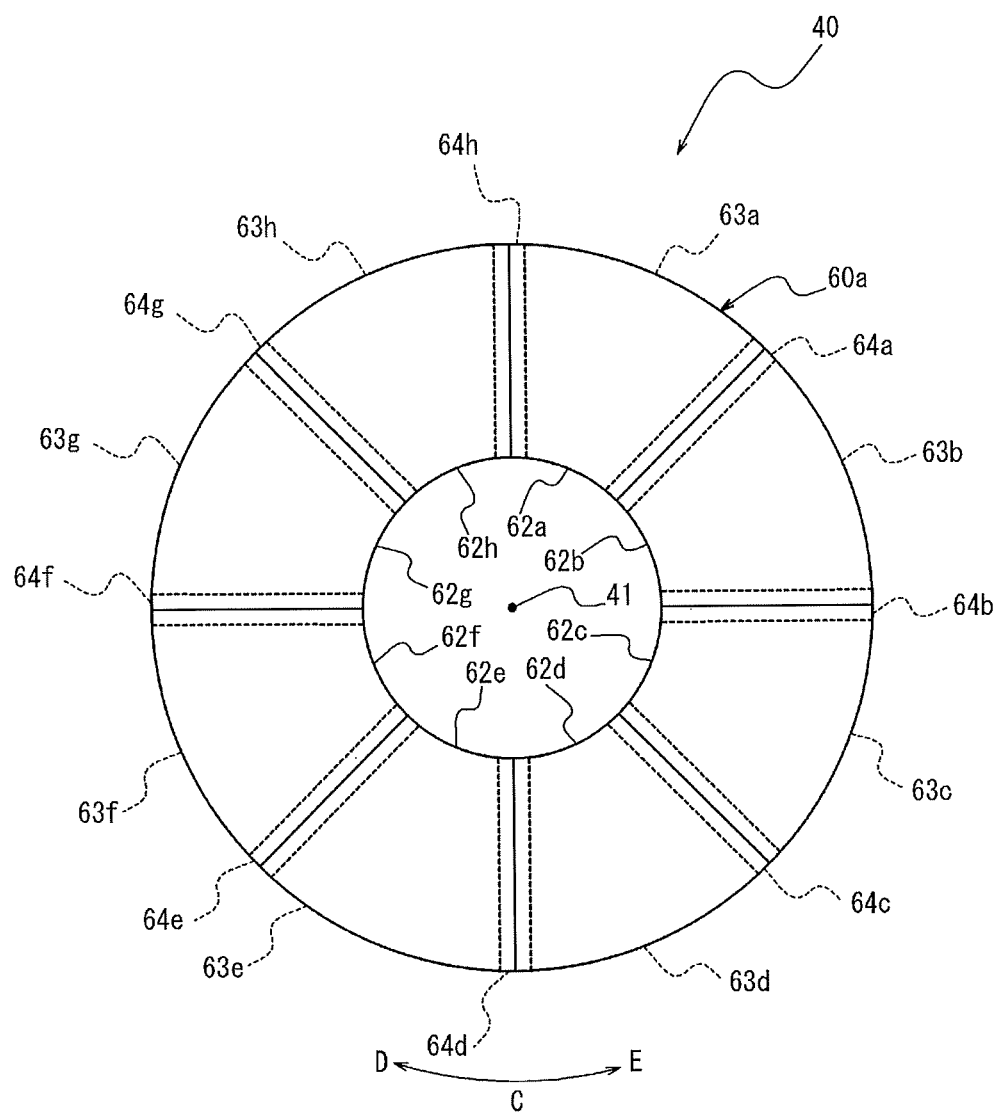
FIG. 9 is a view illustrating a detection region according to a modification of the position acquisition unit illustrated in FIG. 3.

FIG. 9 is a view illustrating an arrangement of detection regions as position information that can be acquired by a position acquisition unit 60a as a modification of the position acquisition unit 60. Similarly to the position acquisition unit 60, the position acquisition unit 60a can acquire position information based on the position on the operation reception unit 40 of a detection target such as an operator's fingertip that comes in contact with or in proximity to the operation reception unit 40. The position acquisition unit 60a acquires position information over time. Specifically, the position acquisition unit 60a acquires position information at a predetermined acquisition timing. The predetermined acquisition timing at which the position acquisition unit 60a acquires the position information is similar to the predetermined acquisition timing at which the position acquisition unit 60 acquires the position information. The position acquisition unit 60a outputs the acquired position information to the control unit 24.

The position acquisition unit 60a of this example includes a capacitance type position detection sensor, for example. The position acquisition unit 60a of the present example includes a plurality of detection units, for example, eight detection units 62a to 62h, which are arranged without a gap in the circumferential direction C around the center point 41 on the operation reception unit 40. Each of the eight detection units 62a to 62h is a detection unit such as a touch pad that can detect the contact made by the detection target.

As illustrated in FIG. 9, the position acquisition unit 60a has eight stable detection regions 63a to 63h as detection regions at positions corresponding to the eight detection units 62a to 62h, respectively. The position acquisition unit 60a has eight boundary detection regions 64a to 64h as detection regions between any two stable detection regions adjacent to each other in the circumferential direction C, from the eight stable detection regions 63a to 63h. That is, the position acquisition unit 60a has 16 detection regions in the example illustrated in FIG. 9. The stable detection regions and the boundary detection regions are alternately arranged in the circumferential direction C. For example, the boundary detection region 64a is arranged at a position adjacent to the stable detection region 63a in the first circumferential direction D. The eight stable detection regions 63a to 63h are regions included in the eight detection units 62a to 62h, respectively. The eight boundary detection regions 64a to 64h are regions each covering two adjacent detection units from the eight detection units 62a to 62h. While the case illustrated in FIG. 9 is an example in which there are eight detection units, eight stable detection regions, and eight boundary detection regions, it is sufficient that these may be provided in plurality, that is, two or more. In the example illustrated in FIG. 9, the stable detection region and the boundary detection region as the detection regions are not arranged in the predetermined region in the vicinity of the center including the center point 41 of the operation reception unit 40. However, at least one of a stable detection region or a boundary detection region as a detection region may be arranged in a predetermined region in the vicinity of the center including the center point 41 of the operation reception unit 40.

Figure 10:
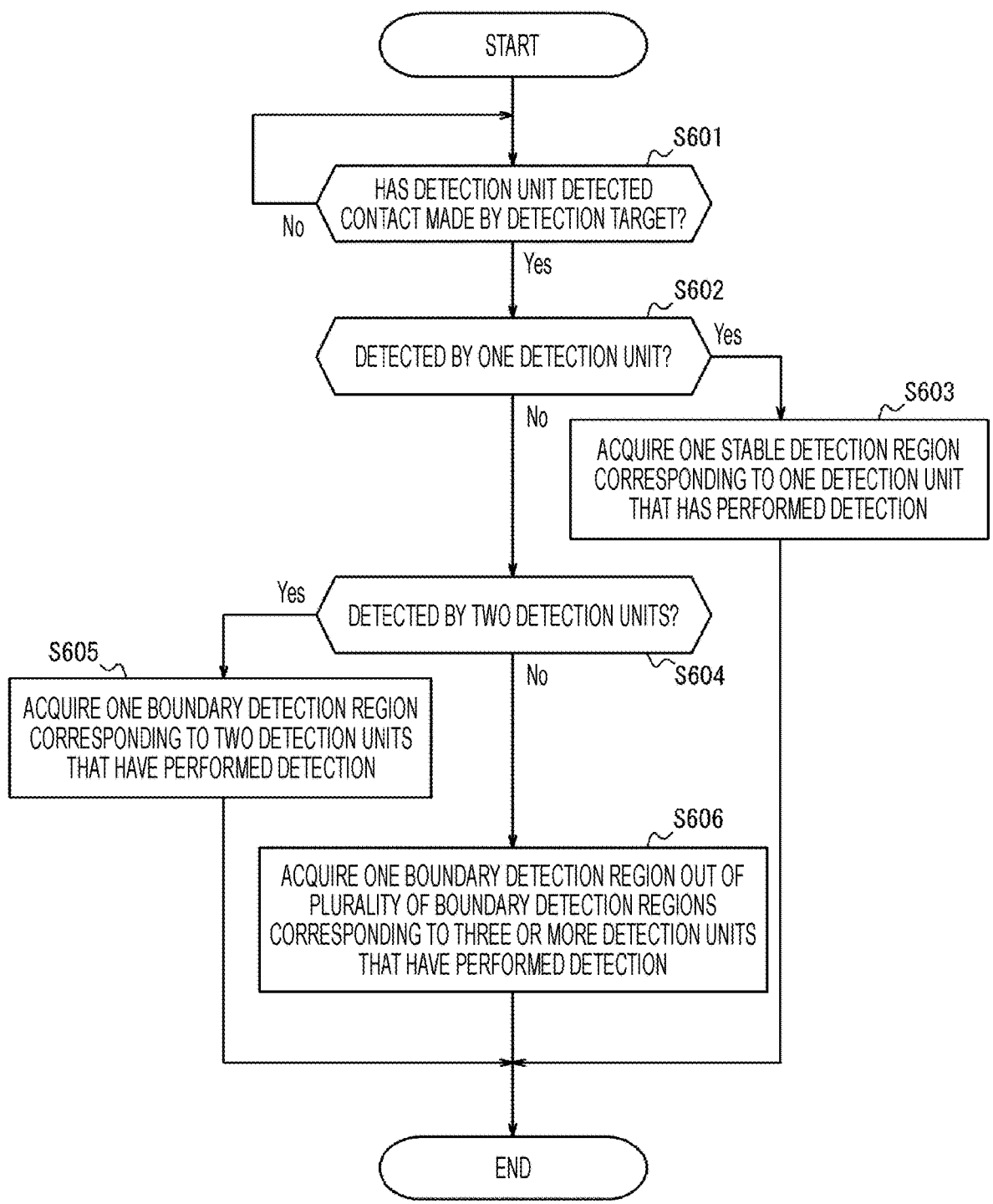
FIG. 10 is a flowchart illustrating a detection region acquisition process according to the position acquisition unit illustrated in FIG. 9.

FIG. 10 is a flowchart illustrating a detection region acquisition process according to the position acquisition unit 60a. As illustrated in FIG. 10, first, the position acquisition unit 60a determines whether at least one of the eight detection units 62*a* to 62*h* has detected a contact made by the detection target (step 601). The following description assumes that in a case where a plurality of detection units detects a contact made by a detection target, the plurality of detection units is continuously arranged in the circumferential direction C and simultaneously detects the contact made by the detection target. The position acquisition unit 60*a* returns to the process of step S601 in a case where none of the detection units detects a contact made by the detection target (No in step S601). In contrast, in a case where any of the detection units detects detection of the detection target (Yes in step S601), the position acquisition unit 60*a* proceeds to the process of step S602.

The position acquisition unit 60*a* determines whether the contact made by the detection target has been detected by one detection unit (step S602). In a case where the position acquisition unit 60*a* determines that one detection unit has detected the contact made by the detection target (Yes in step S602), the position acquisition unit 60*a* acquires one stable detection region corresponding to the one detection unit, as the position information of the detection target (step S603). For example, in a case where the detection unit 62*a* has detected the contact made by the detection target, the position acquisition unit 60*a* acquires the stable detection region 63*a* corresponding to the detection unit 62*a*, as the position information of the detection target.

In a case where the position acquisition unit 60*a* determines that a number of detection units that detected the contact made by the detection target is not one (No in step S602), the position acquisition unit 60*a* determines whether the contact made by the detection target has been detected by two detection units adjacent in the circumferential direction C (step S604). In a case where the position acquisition unit 60*a* determines that two detection units have detected the contact made by the detection target (Yes in step S604), the position acquisition unit 60*a* acquires one boundary detection region corresponding to the two detection units, as the position information of the detection target (step S605). Specifically, the position acquisition unit 60*a* acquires one boundary detection region arranged between two stable detection regions corresponding to the two detection units, respectively, as the position information of the detection target. For example, in a case where the detection unit 62*a* and the detection unit 62*b* have detected the contact made by the detection target, the position acquisition unit 60*a* acquires the boundary detection region 64*a* located between the stable detection region 63*a* corresponding to the detection unit 62*a* and the stable detection region 63*b* corresponding to the detection unit 62*b*, as the position information of the detection target.

In a case where the position acquisition unit 60*a* determines that the contact made by the detection target has been detected not by both one detection unit and two detection units (No in step S602 and No in step S604), that is, in a case where three or more detection units continuously arranged in the circumferential direction C have detected the contact made by the detection target simultaneously, the position information 60*a* acquires one boundary detection region from a plurality of boundary detection regions corresponding to the three or more detection units, as the position information of the detection target (step S606). For example, in a case where the detection unit 62*a*, the detection unit 62*b*, and the detection unit 62*c* have detected the contact made by the detection target, the position acquisition unit 60*a* acquires one of the boundary detection region 64*a* corresponding to the detection unit 62*a* and the detection unit 62*b*, or the boundary detection region 64*b* corresponding to the detection unit 62*b* and the detection unit 62*c*, as the position information of the detection target. The boundary detection region to be acquired can be determined on the basis of the direction in the circumferential direction C having a temporal change of the acquired detection region until the immediately preceding time, for example. Specifically, it is allowable to acquire a boundary detection region located at a most distal end side in the circumferential direction C having a temporal change of the acquired detection region until the immediately preceding time, from the boundary detection regions to be acquired.

As described above, according to the position acquisition unit 60*a* of the present example, it is possible to use a configuration having a larger number of detection regions than the number of detection units, for example, the number of detection regions that is twice the number of detection units. Furthermore, even in a case where the detection target comes in contact with the plurality of detection units, it is possible to acquire one specific detection region of the detection target.

Meanwhile, when the position acquisition unit 60*a* is used, in a case where the detection target such as the operator's fingertip is located near the boundary between adjacent detection units, there might be cases where which of the boundary detection region and two stable detection regions adjacent to the boundary detection region is to be acquired as the position information will not be stable. When the set value is increased or decreased sequentially following the change in the temporarily acquired position information in this situation, for example, and in a case where the operator rotates a finger as the operation target in one direction of the circumferential direction C, there might be a case where the movement of position information in a direction opposite to the direction intended by the operator is detected at a timing when the operator releases the finger. In view of this, a set value increase/decrease process for suppressing such false detection will be described below.

Figure 11:
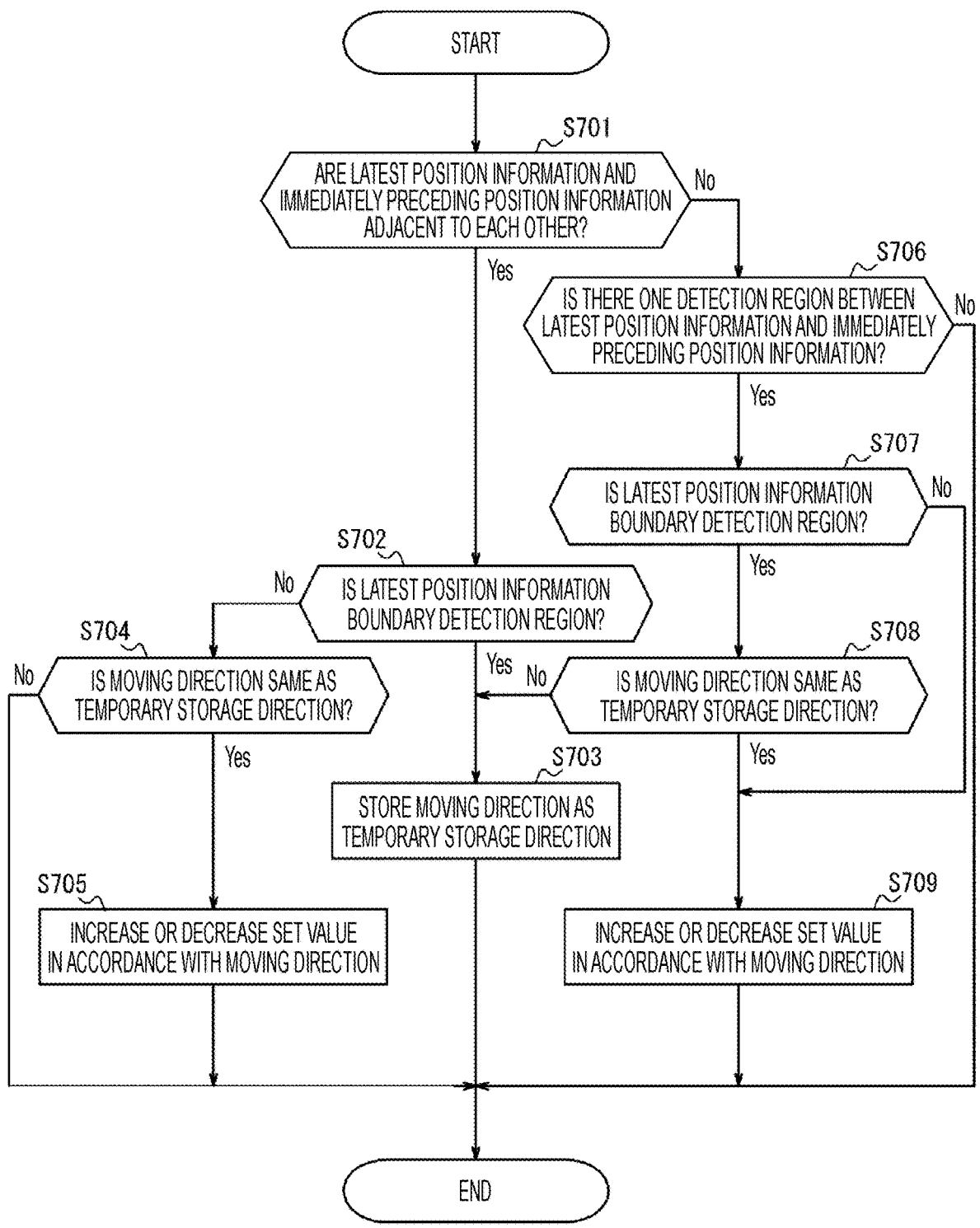
FIG. 11 is a flowchart illustrating set value increase/decrease process to be executed by the syringe pump in FIG. 1 in a case where the syringe pump includes the position acquisition unit illustrated in FIG. 9.

FIG. 11 is a flowchart illustrating a set value increase/decrease process executed by the syringe pump 1 in a case where the syringe pump 1 includes a position acquisition unit 60*a* instead of the position acquisition unit 60. In the set value increase/decrease process illustrated in FIG. 11, the position acquisition unit 60*a* acquires position information of the detection target over time. Specifically, the position acquisition unit 60*a* acquires position information at an acquisition timing occurring at a predetermined period. The position acquisition unit 60*a* acquires position information every 10 milliseconds, for example.

As illustrated in FIG. 11, the control unit 24 determines whether latest position information acquired at a latest acquisition timing and immediately preceding position information acquired at an immediately preceding acquisition timing are two detection regions adjacent in the circumferential direction C (step S701). Here, the stable detection regions and the boundary detection regions are alternately arranged in the circumferential direction C in the position acquisition unit 60*a*. Therefore, in a case where the latest position information and the immediately preceding position information are two detection regions adjacent in the circumferential direction, one of the latest position information or the immediately preceding position information is a stable detection region, and the other is a boundary detection region.

In a case where the control unit 24 determines that the latest position information and the immediately preceding position information are two detection regions adjacent in the circumferential direction (Yes in step S701), the control unit 24 determines whether the latest position information is a boundary detection region (step S702). In a case where the control 24 determines that the latest position information is a boundary detection region (Yes in step S702), that is, in a case where the control unit 24 determines that the immediately preceding position information is a stable detection region and the latest position information is a boundary detection region, the control unit 24 stores a direction in which the latest position information is located with respect to the immediately preceding position information (hereinafter referred to as "moving direction" as appropriate) in the storage unit 23 as a temporary storage direction (step S703). For example, in a case where the immediately preceding position information is the stable detection region 63a and the latest position information is the boundary detection region 64a, the control unit 24 stores the first circumferential direction D in which the boundary detection region 64a is located with respect to the stable detection region 63a in the storage unit 23 as a temporary storage direction.

In contrast, in the process of step 702, in a case where the control unit 24 determines that the latest position information is the stable detection region (No in step S702), that is, in a case where the immediately preceding position information is the boundary detection region and the latest position information is the stable detection region, the control unit 24 determines whether the moving direction is the same as the temporary storage direction stored in the storage unit 23 (step S704). After the control unit 24 determines that the moving direction is the same as the temporary storage direction (Yes in step S704), the control unit 24 increases or decreases the set value in accordance with the moving direction (step S705). For example, in a case where the immediately preceding position information is the boundary detection region 64a and the latest position information is the stable detection region 63b, and when the first circumferential direction D that is the moving direction is the same as the temporary storage direction, the control unit 24 increases the set value, for example, in accordance with the first circumferential direction D. When it is determined that the moving direction is different from the temporary storage direction (No in step S704), the control unit 24 will not perform the process.

In the process of step S701, in a case where the control unit 24 determines that the latest position information and the immediately preceding position information are not two detection regions adjacent in the circumferential direction (No in step S701), the control unit 24 determines whether one detection region exists between the latest position information and the immediately preceding position information (step S706). Here, in a case where one detection region exists between the latest position information and the immediately preceding position information, the latest position information and the immediately preceding position information are both stable detection regions, or the latest positional information and the immediately preceding position are both boundary detection regions.

In a case where the control unit 24 determines that one detection region exists between the latest position information and the immediately preceding position information (Yes in step S706), the control unit 24 determines whether the latest position information is a boundary detection region (step S707). In a case where the control unit 24 determines that the latest position information is the boundary detection region (Yes in step S707), that is, in a case where the control unit 24 determines that both the latest position information and the immediately preceding position information are boundary detection regions, the control unit 24 determines whether the moving direction is the same as the temporary storage direction stored in the storage unit 23 (step S708). After the control unit 24 determines that the moving direction is the same as the temporary storage direction (Yes in step S708), the control unit 24 increases or decreases the set value in accordance with the moving direction (step S709). For example, in a case where the immediately preceding position information is the boundary detection region 64a and the latest position information is the boundary detection region 64b, and when the first circumferential direction D that is the moving direction is the same as the temporary storage direction, the control unit 24 increases the set value, for example, in accordance with the first circumferential direction D. After the control unit 24 determines that the moving direction is different from the temporary storage direction (No in step S708), the control unit 24 stores the moving direction in the storage unit 23 as the temporary storage direction (step S703). For example, in a case where the immediately preceding position information is the boundary detection region 64a and the latest position information is the boundary detection region 64b, the control unit 24 determines that the first circumferential direction D being the moving direction is different from the temporary storage direction, and then, stores the first circumferential direction D, which is the direction in which the boundary detection region 64b is located with respect to the boundary detection region 64a, in the storage unit 23 as a temporary storage direction.

In contrast, in a case where the control unit 24 determines that the latest position information is the stable detection region (No in step S707), that is, in a case where the control unit 24 determines that both the latest position information and the immediately preceding position information are the stable detection regions, the control unit 24 increases or decreases the set value in accordance with the moving direction (step S709). For example, in a case where the immediately preceding position information is the stable detection region 63b and the latest position information is the stable detection region 63a, the control unit 24 decreases the set value, for example, in accordance with the second circumferential direction E being the moving direction.

In the process of step S706, in a case where the control unit 24 determines that there are two or more detection regions between the latest position information and the immediately preceding position information (No in step S706), the control unit 24 will not perform the process.

As described above, according to the set value increase/decrease process illustrated in FIG. 11, false detection caused by using the position acquisition unit 60a can be suppressed. In the syringe pump 1 including the position acquisition unit 60, the above-described set value increase/decrease process can be similarly executed when it is assumed that the detection regions 61a to 61h are alternately arranged with the stable detection region and the boundary detection region.

The control unit 24 may not change the set value in a case where the acquired position information has not changed for a predetermined time, unless the subsequent acquired position information moves by a predetermined distance or more within a predetermined time. For example, in a case where the acquired position information has not changed for a predetermined time, the control unit 24 may set a set value increase/decrease stop mode described below. The predetermined time in the present process is 1.5 seconds, for example. The predetermined distance in the present process is a half circumference in the circumferential direction C (refer to FIG. 3), for example. With such a control, the syringe pump 1 can help suppress the occurrence of false detection.

Figure 12:
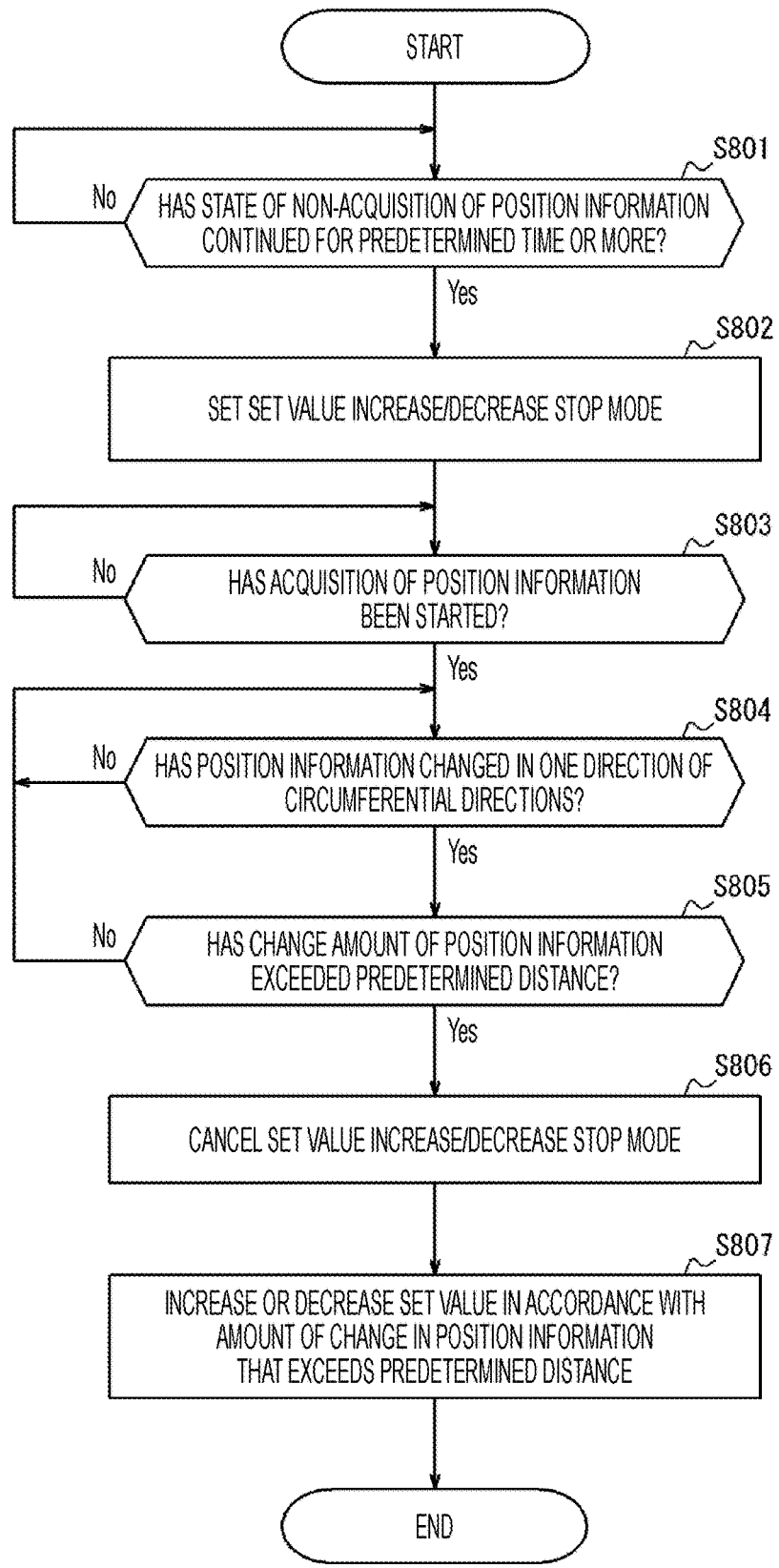
FIG. 12 is a flowchart illustrating dead zone control executed by the syringe pump illustrated in FIG. 1.

FIG. 12 is a flowchart illustrating dead zone control executed by the syringe pump 1. As illustrated in FIG. 12, the control unit 24 determines whether a state in which position information is not acquired for a predetermined time or greater continues (step S801). Specifically, the control unit 24 uses the clocking unit 22 to measure the time when the position information is not acquired and determines whether the time measured reaches a predetermined time. When the control unit 24 determines no continuation of the state where the position information is not acquired for a predetermined time or greater (No in step S801), the control unit 24 returns to the process of step S801. For example, in a case where the position information is acquired before a predetermined time elapses, the control unit 24 resets the clocking by the clocking unit 22.

After the control unit 24 determines continuation of the state where the position information has not been acquired for a predetermined time or more (Yes in step S801), the control unit 24 sets the set value increase/decrease stop mode (step S802). The set value increase/decrease stop mode is a mode in which increase/decrease of the set value is stopped until the amount of change in the position information exceeds a predetermined distance, and this mode is implemented by steps S803 to S807 described below.

Thereafter, the control unit 24 determines whether acquisition of position information has started (step S803). In a case where acquisition of position information is not started (No in step S803), the process returns to step S803.

When the control unit 24 determines that the acquisition of the position information has started (Yes in step S803), the control unit 24 determines whether the position information has started to change in one direction of the circumferential direction C (step S804). In a case where the position information does not start to change in one direction of the circumferential direction C (No in step S804), the process returns to step S804.

When the control unit 24 determines that the position information has started to change in one direction of the circumferential direction C (Yes in step S804), the control unit 24 starts a measurement of the amount of change in the position information in one direction of the circumferential direction C, and determines whether the amount of change in the position information exceeds a predetermined distance (step S805). In a case where the amount of change in the position information does not exceed the predetermined distance (No in step S805), the process returns to step S804.

In a case where the amount of change in the position information exceeds the predetermined distance (Yes in step S805), the control unit 24 cancels the set value increase/decrease stop mode (step 806). For example, in a case where the acquired position information exceeds a half circumference in the circumferential direction C (for example, in a case where the acquired detection region has changed from the detection region 61a to the detection region 61f in the first circumferential direction D), the set value increase/decrease stop mode will be canceled. Furthermore, the control unit 24 increases or decreases the set value in accordance with the amount of change in the position information that exceeds the predetermined distance (step S807). That is, the amount of change in the position information that has changed to a predetermined distance in one direction of the circumferential direction C will not be reflected in the increase/decrease of the set value.

As described above, according to the dead zone control illustrated in FIG. 12, in a case where the position information has not been acquired for a predetermined time or greater, it is possible to stop increase/decrease of the set value until the position information exceeds a predetermined distance in one direction of the circumferential direction. Therefore, erroneous operation caused by operator's erroneous touch (or touching) on the position acquisition unit 60 can be suppressed. The dead zone control illustrated in FIG. 12 can be similarly executed even in a case where the syringe pump 1 includes the position acquisition unit 60a instead of the position acquisition unit 60.

The control unit 24 may increase or decrease the set value at a speed proportional to the moving speed of the acquired position information. Alternatively, the control unit 24 may perform control so that the higher the moving speed of the acquired position information, the higher the speed of change in the set value with respect to the moving speed of the acquired position information.

Configuration of Operation Reception Unit

Figure 13:
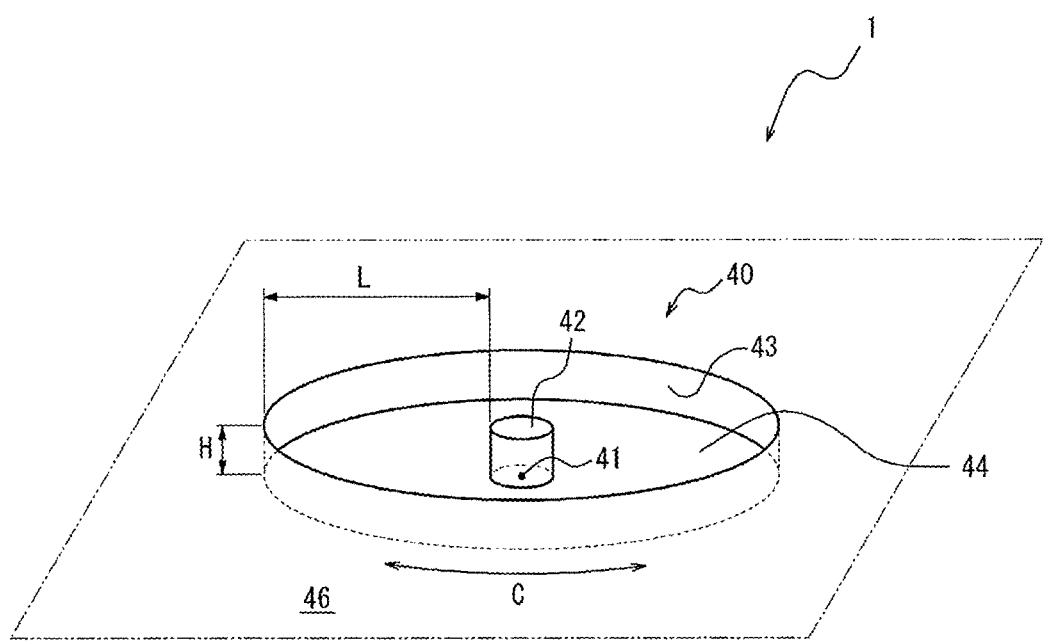
FIG. 13 is a schematic view illustrating a configuration of an operation reception unit provided in the syringe pump illustrated in FIG. 1.

FIG. 13 is a schematic view illustrating a configuration of the operation reception unit 40. As illustrated in FIG. 13, the operation reception unit 40 includes an annular recess. Specifically, the operation reception unit 40 of the present embodiment includes a protrusion 42, a circumferential wall 43, and a bottom 44. The protrusion 42 protrudes at a position corresponding to the center point 41. The circumferential wall 43 is configured by a circumferential surface that is spaced apart from the protrusion 42 and extends in the circumferential direction C around the center point 41. The bottom 44 is located between the protrusion 42 and the circumferential wall 43. In the present embodiment, the edge of the circumferential wall 43 is flush (i.e., even) with the surface of the housing 46. The operation reception unit 40 is preferably a product integrally molded with the housing 46 from the viewpoint of improving the cleanability in addition to suppressing the deterioration in operability.

A height H of the circumferential wall 43, for example, is preferably 15% to 45% of a shortest distance (i.e., straight line) L between the circumferential wall 43 and the protrusion 42 (i.e., H is equal to 15% to 45% of L). With this size of the operation reception unit 40, it is possible to smoothly move the fingertip of the operator as a detection target in the circumferential direction C on the bottom 44 between the circumferential wall 43 and the protrusion 42 without being blocked by the circumferential wall 43.

Due to the protrusion 42, the position acquisition unit 60 does not detect the position information of the detection target in the vicinity of the center point 41. Therefore, it is possible to suppress simultaneous acquisition of a plurality of detection regions that is not adjacent in the circumferential direction C, as acquired detection regions, by the position acquisition unit 60. In a case where the position acquisition unit 60 is implemented with a capacitance type position detection sensor, it is possible to avoid providing a detection region in the vicinity of the center point 41, thereby making it possible to suppress simultaneous acquisition of a plurality of detection regions not adjacent in the circumferential direction C, as the acquired detection region.

Figure 14:
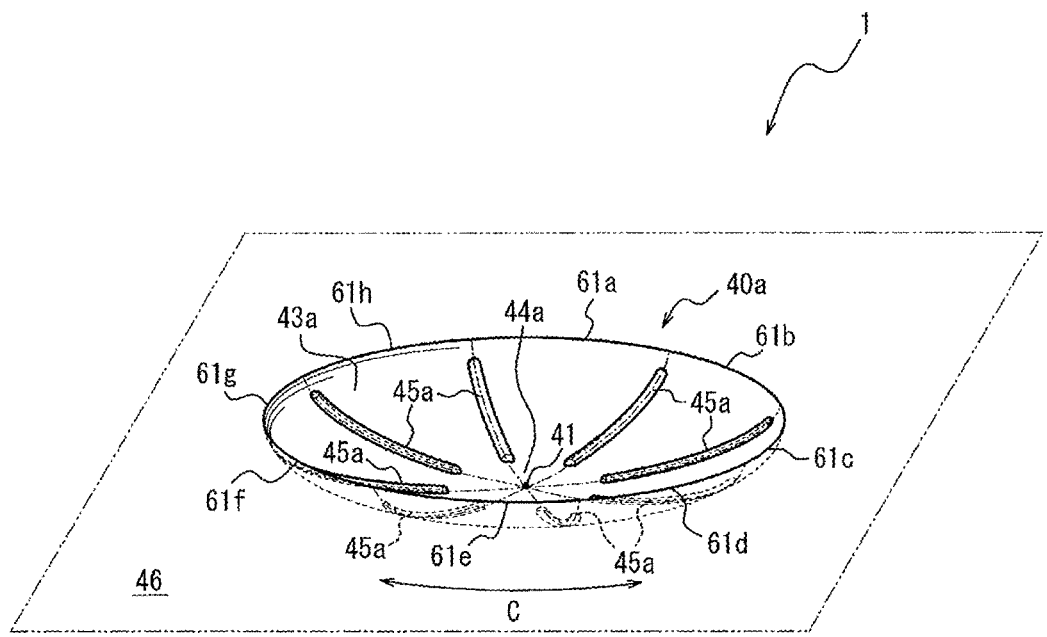
FIG. 14 is a schematic view illustrating a configuration of a first modification of the operation reception unit provided in the syringe pump illustrated in FIG. 1.

FIG. 14 is a schematic view illustrating a configuration of an operation reception unit 40a as a first modification of the operation reception unit 40. As illustrated in FIG. 14, the operation reception unit 40a is configured by a substantially spherical dome-shaped curved recess. Specifically, the operation reception unit 40a includes a circumferential wall 43a and a bottom 44a. The circumferential wall 43a includes a circumferential surface extending in the circumferential direction C around the center point 41, having a curved concave surface smoothly connected to the bottom 44a. The edge of the circumferential wall 43a is flush (i.e., even) with the surface of the housing 46. Similarly to the operation reception unit 40, the operation reception unit 40a is preferably a product integrally molded with the housing 46 from the viewpoint of improving the cleanability in addition to suppressing the deterioration in operability.

In the operation reception unit 40a, a surface of at least one of the circumferential wall 43a or the bottom 44a includes a partition 45a formed at a position corresponding to each of boundary lines of the plurality of detection regions 61a to 61h adjacent in the circumferential direction C. The partition 45a is a linear protrusion protruding along each of the boundary lines of the plurality of detection regions 61a to 61h adjacent in the circumferential direction C. The partition 45a may be a linear groove recessed along each of the boundary lines of the plurality of detection regions 61a to 61h adjacent in the circumferential direction C.

As described above, for example, in a case where the operator's fingertip as a detection target is moved in the circumferential direction C on the circumferential wall 43 or the bottom 44, using the operation reception unit 40a in which the partition 45a is formed allows the fingertip to come in contact with the partition 45a each time the fingertip moves to the adjacent detection region. With this configuration, the operation reception unit 40a gives the operator a tactile sensation from the contact of the fingertip with the partition 45a and thereby can give the operator recognition of the increase/decrease of the minimum unit of the set value, making it possible to facilitate fine adjustment of the set value.

Figure 15:
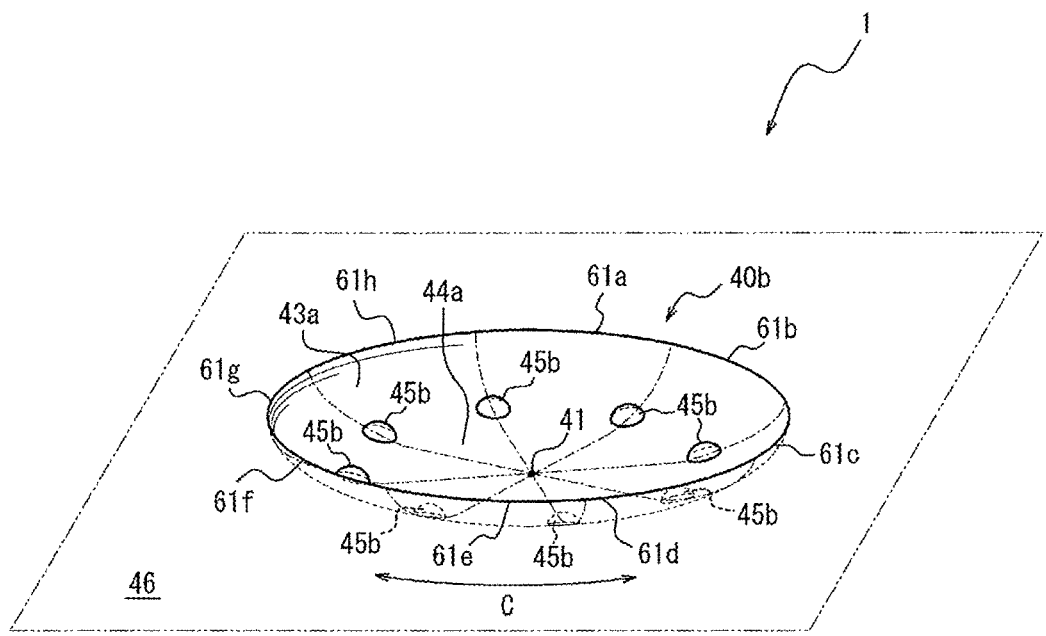
FIG. 15 is a schematic view illustrating a configuration of a second modification of the operation reception unit provided in the syringe pump illustrated in FIG. 1.

The shape of the partition 45a is not particularly limited as long as it is possible to give the operator a tactile sensation due to the contact of the fingertip with the partition. For example, FIG. 15 is a schematic view illustrating a configuration of an operation reception unit 40b as a second modification of the operation reception unit 40. The operation reception unit 40b has a configuration similar to that of the operation reception unit 40a except that a partition 45b is formed instead of the partition 45a. As illustrated in FIG. 15, in the operation reception unit 40b, a surface of at least one of the circumferential wall 43a or the bottom 44a includes a partition 45b formed at a position corresponding to each of boundary lines of the plurality of detection regions 61a to 61h adjacent in the circumferential direction C. The partition 45b is a substantially spherical dome-shaped protrusion that is located on each of the boundary lines of the plurality of detection regions 61a to 61h adjacent in the circumferential direction C. The partition 45b may be a substantially spherical dome-shaped recess positioned on each of the boundary lines of the plurality of detection regions 61a to 61h adjacent in the circumferential direction C. The operation reception unit 40b can provide effects similar to those of the operation reception unit 40a described above.

The present disclosure is not limited to the configuration specified in each of the above-described embodiments, and various modifications can be made without departing from the scope and spirit described in the claims. For example, the functions included in each of components, steps, or the like can be rearranged in a range that causes no logical contradiction, and a plurality of components, steps, or the like can be incorporated or further divided.

While the present embodiment has described the process of increasing or decreasing the set value on the basis of the temporal change in the acquired position information has been described as the process of the syringe pump 1, the present disclosure is not limited to such a process. The process of the syringe pump 1 may be any process that identifies an operation input by the detection target, for example, switching a selection item on the basis of the temporal change of the acquired position information.

While the present embodiment has described a case where the medical device is implemented as a syringe pump, the medical device is not limited to this. Examples of other medical devices include liquid delivery devices such as infusion pumps, nutrient pumps, and blood pumps, ultrasound image diagnostic devices, and optical image diagnostic devices.

The detailed description above describes embodiments of a medical device, and more particularly to a medical device that receives operation input by an operator. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
an operation reception unit;
a position acquisition unit configured to acquire position information of a detection target that is in contact with or proximity to the operation reception unit, the acquired position information being based on a position on the operation reception unit of the detection target;
a control unit configured to identify an operation input by the detection target based on a change in the acquired position information, the control unit configured to increase or decrease a predetermined set value based on a change in the acquired position information in a circumferential direction around a predetermined center point on the operation reception unit;
the control unit configured to increase the set value where the acquired position information changes in a first circumferential direction that is one direction of the circumferential direction and to decrease the set value where the acquired position information changes in a second circumferential direction that is a direction opposite to the first circumferential direction;
the position acquisition unit including a plurality of detection units arranged in the circumferential direction, and where one detection unit from the plurality of detection units is configured to detect a contact made by the detection target, the position acquisition unit configured to acquire a stable detection region as a detection region of a position corresponding to the one detection unit, as the position information of the detection target;
where two detection units adjacent in the circumferential direction from the plurality of detection units simultaneously detect a contact made by the detection target, the position acquisition unit is configured to acquire a boundary detection region as a detection region between two stable detection regions corresponding to the two detection units, respectively, as the position information of the detection target;
a storage unit configured to store one of the first circumferential direction or the second circumferential direction as a temporary storage direction;

the position acquisition unit configured to acquire the position information at an acquisition timing occurring at a predetermined period;

where latest position information acquired at a latest acquisition timing and immediately preceding position information acquired at an immediately preceding acquisition timing are two detection regions adjacent in the circumferential direction and where the latest position information is the stable detection region, and when a moving direction being a direction of the latest position information with respect to the immediately preceding position information is the same as the temporary storage direction, the control unit configured to increase or decrease the set value in accordance with the moving direction; and where the latest position information is the boundary detection region, the control unit performs control to store the moving direction in the storage unit as the temporary storage direction.

2. The medical device according to claim 1, wherein the control unit is configured to increase or decrease the set value in accordance with a direction of an immediately preceding change in the acquired position information from the first circumferential direction or the second circumferential direction where the acquired position information has not changed for a predetermined time or longer.

3. The medical device according to claim 2, wherein the control unit is configured to increase or decrease the set value with an amount of change per unit time corresponding to an amount of change per unit time of the position information with an immediately preceding change where the acquired position information has not changed for a predetermined time or longer.

4. The medical device according to claim 1, wherein the control unit is not to change the set value until subsequent acquired position information changes by a predetermined amount or longer where the direction of change in the acquired position information is switched from one of the first circumferential direction or the second circumferential direction, to the other direction.

5. The medical device according to claim 1, wherein the position acquisition unit includes a plurality of detection regions arranged in the circumferential direction, and is configured to acquire a detection region which the detection target is in contact with or in closest proximity, from the plurality of detection regions, as the position information of the detection target.

6. The medical device according to claim 5, wherein, where the detection region as the position information acquired at the latest acquisition timing is different from the detection region as the position information acquired at the immediately preceding acquisition timing, the control unit is configured to determine that the position information has changed in a direction in which a distance in the circumferential direction from the immediately preceding detection region to the latest detection region is shorter from the first circumferential direction and the second circumferential direction, and to increase or decrease the set value.

7. The medical device according to claim 5, wherein the operation reception unit includes:
a bottom;
a circumferential wall formed with a circumferential surface extending along a circumferential direction around the center point and curved to have a recessed surface to be connected to the bottom; and
a surface of at least one of the circumferential wall or the bottom has a partition at a position corresponding to each of boundary lines of the plurality of detection regions.

8. The medical device according to claim 1, wherein, where there is one detection region between the latest position information and the immediately preceding position information, and where the latest position information is the stable detection region, the control unit is configured to increase or decrease the set value in accordance with the moving direction; and where the latest position information is the boundary detection region, and when the moving direction is the same as the temporary storage direction, the control unit is configured to increase and decrease the set value in accordance with the moving direction.

9. The medical device according to claim 1, wherein, where the position acquisition unit has acquired the position information only within a predetermined time, the control unit is configured to change a unit of increase/decrease of the set value based on a change in the position information in a subsequent acquisition.

10. The medical device according to claim 1, wherein, where the position acquisition unit cannot acquire the position information, the control unit would not use the previously acquired position information for increase/decrease of the set value.

11. The medical device according to claim 1, wherein, where the position information has not changed for a predetermined time, the control unit stops increase/decrease of the set value until the amount of change in the position information exceeds a predetermined distance.

12. The medical device according to claim 1, wherein, where the position information changes beyond a predetermined distance in one direction of the circumferential direction after the acquisition of the position information is started, the control unit is configured to increase or decrease the set value in accordance with the amount of change exceeding the predetermined distance.

13. The medical device according to claim 1, wherein the operation reception unit includes a protrusion that protrudes at a position corresponding to the center point.

14. The medical device according to claim 13, wherein the operation reception unit includes a circumferential wall protruding along a circumferential direction around the center point.

15. The medical device according to claim 14, wherein a height of the circumferential wall is 15% to 45% with respect to a distance between the circumferential wall and the protrusion.

16. The medical device according to claim 1, wherein the operation reception unit is a product integrally molded with a housing.

* * * * *